United States Patent
Vasmatzis et al.

(10) Patent No.: US 8,338,109 B2
(45) Date of Patent: Dec. 25, 2012

(54) PREDICTING CANCER OUTCOME

(75) Inventors: George Vasmatzis, Byron, MN (US); John C. Cheville, Pine Island, MN (US); Farhad Kosari, Rochester, MN (US); Cemile Dilara Savci Heijink, Amsterdam (NL); Jan-Marie Willard Munz, Oronoco, MN (US); Eric W. Klee, Rochester, MN (US); Lori Tillmans, Stanton, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 468 days.

(21) Appl. No.: 12/513,329

(22) PCT Filed: Nov. 2, 2007

(86) PCT No.: PCT/US2007/083504
§ 371 (c)(1),
(2), (4) Date: Jan. 28, 2010

(87) PCT Pub. No.: WO2008/058018
PCT Pub. Date: May 15, 2008

(65) Prior Publication Data
US 2010/0130377 A1 May 27, 2010

Related U.S. Application Data

(60) Provisional application No. 60/856,536, filed on Nov. 2, 2006.

(51) Int. Cl.
*G01N 33/53* (2006.01)
(52) U.S. Cl. ........................................ 435/7.1
(58) Field of Classification Search .................. None
See application file for complete search history.

(56) References Cited

U.S. PATENT DOCUMENTS

| | | | |
|---|---|---|---|
| 5,143,854 A | 9/1992 | Pirrung et al. | |
| 5,744,305 A | 4/1998 | Fodor et al. | |
| 6,630,358 B1 | 10/2003 | Wagner et al. | |
| 2002/0182586 A1 | 12/2002 | Morris et al. | |
| 2005/0202442 A1 | 9/2005 | Morris et al. | |
| 2006/0211017 A1* | 9/2006 | Chinnaiyan et al. | 435/6 |
| 2007/0048738 A1* | 3/2007 | Donkena et al. | 435/6 |
| 2009/0149333 A1 | 6/2009 | Knudsen et al. | |

FOREIGN PATENT DOCUMENTS

| | | |
|---|---|---|
| WO | WO 02/00929 A1 | 1/2002 |
| WO | WO 03/012067 A2 | 2/2003 |
| WO | WO 2006/135596 A2 | 12/2006 |
| WO | WO 2007/070621 A2 | 6/2007 |
| WO | WO 2009/045115 A1 | 4/2009 |
| WO | WO 2007/056049 A2 | 5/2009 |

OTHER PUBLICATIONS

Noordzij et al (Clin Cancer Res, 1997, 3: 805-815).*
Noordzij et al (Clin Cancer Res, 1997, 3: 805-815).*
Tockman et al (Cancer Res., 1992, 52:2711s-2718s).*
Bostwick et al., "Prognostic factors in prostate cancer: College of American Pathologists consensus statement," Arch Pathol Lab Med, 2000, 124(7):995-1000.
DeMichelis et al., "TMPRSS2:ERG gene fusion associated with lethal prostate cancer in a watchful waiting cohort," Oncogene, 2007, 26(31):4596-4599.
Epstein et al., "Prognostic factors and reporting of prostate carcinoma in radical prostatectomy and pelvic lymphadenectomy specimens," Scand. J. Urol. Nephrol. Suppl., 2005, 216:34-63.
Gleason, "Histologic grading and clinical staging of prostatic carcinoma," Urologic pathology: the prostate, (Tannenbaum, ed.) Lea & Febiger, Philadelphia, PA, pp. 171-197.
Gleason, "Histologic grading of prostate cancer: a perspective," Hum. Pathol., 1992, 23(3):273-279.
Humphrey et al., "Histologic grade, DNA ploidy, and intraglandular tumor extent as indicators of tumor progression of clinical Stage B prostatic carcinoma," Am J Surg Pathol, 1991, 15(12):1165-1170.
Robertson and Paulson, "DNA in radical prostatectomy specimens. Prognostic value of tumor ploidy," Acta Oncol, 1991, 30(2):205-207.
Winkler et al., "Stage D1 prostatic adenocarcinoma: significance of nuclear DNA ploidy patterns studied by flow cytometry," Mayo Clin Proc, 1988, 63(2):103-112.
Zanetta et al., "Flow-cytometric analysis of deoxyribonucleic acid content in advanced ovarian carcinoma: its importance in long-term survival," Am J Obstet Gynecol, 1996, 175(5):1217-1225.
International Search Report/Written Opinion in PCT/US2007/83504 mailed Apr. 14, 2008, 3 pages.
International Preliminary Report on Patentability in PCT/US2007/83504 mailed May 5, 2009, 4 pages.
GenBank Accession No. AA462934 dated Jun. 10, 1997.
GenBank Accession No. AA920095 dated Apr. 20, 1998.
GenBank Accession No. AB028840 dated Jan. 12, 2000.
GenBank Accession No. AB030836 dated Oct. 23, 1999.
GenBank Accession No. AB036741 dated Dec. 22, 2000.
GenBank Accession No. AF077349 dated Dec. 14, 2000.
GenBank Accession No. AF077351 dated Dec. 20, 2000.
GenBank Accession No. AF115517 dated Nov. 23, 2005.
GenBank Accession No. AI413910 dated Feb. 9, 1999.
GenBank Accession No. AI414999 dated Feb. 9, 1999.
GenBank Accession No. AI425960 dated Mar. 9, 1999.
GenBank Accession No. AI851940 dated Jul. 15, 1999.
GenBank Accession No. AK018022 dated Sep. 19, 2008.
GenBank Accession No. AK019341 dated Sep. 19, 2008.
GenBank Accession No. AK019342 dated Sep. 19, 2008.
GenBank Accession No. AK034387 dated Sep. 19, 2008.
GenBank Accession No. AK038229 dated Sep. 19, 2008.
GenBank Accession No. AK038434 dated Sep. 19, 2008.
GenBank Accession No. AK041534 dated Sep. 19, 2008.
GenBank Accession No. AK042683 dated Sep. 19, 2008.
GenBank Accession No. AK136096 dated Sep. 19, 2008.

(Continued)

*Primary Examiner* — Sean Aeder
(74) *Attorney, Agent, or Firm* — Fish & Richardson P.C.

(57) ABSTRACT

This document provides methods and materials related to assessing prostate cancer in mammals. For example, this document provides nucleic acids and polypeptides that can be analyzed to determine whether a male mammal having prostate cancer is susceptible to a good or poor outcome.

3 Claims, 12 Drawing Sheets

OTHER PUBLICATIONS

GenBank Accession No. AK136101 dated Sep. 19, 2008.
GenBank Accession No. AK142768 dated Sep. 19, 2008.
GenBank Accession No. AL591433 dated Jan. 15, 2009.
GenBank Accession No. BC004702 dated Jul. 15, 2006.
GenBank Accession No. BC055737 dated Jul. 15, 2006.
GenBank Accession No. BC086799 dated Sep. 21, 2006.
GenBank Accession No. BF449664 dated Dec. 1, 2000.
GenBank Accession No. BG063957 dated Jan. 26, 2001.
GenBank Accession No. BG077309 dated Dec. 17, 2003.
GenBank Accession No. BM114282 dated Jan. 30, 2002.
GenBank Accession No. BY023910 dated Dec. 6, 2002.
GenBank Accession No. CN724527 dated May 18, 2004.
GenBank Accession No. NM_000130 dated Oct. 18, 2009.
GenBank Accession No. NM_000493 dated Mar. 15, 2009.
GenBank Accession No. NM_001034 dated Oct. 5, 2009.
GenBank Accession No. NM_001049 dated Jun. 21, 2009.
GenBank Accession No. NM_001067 dated Oct. 18, 2009.
GenBank Accession No. NM_001786 dated Nov. 1, 2009.
GenBank Accession No. NM_001844 dated Sep. 28, 2009.
GenBank Accession No. NM_003873.3 dated Oct. 18, 2009.
GenBank Accession No. NM_005025.2 dated Jul. 12, 2009.
GenBank Accession No. NM_005651.1 dated Oct. 27, 2009.
GenBank Accession No. NM_006558 dated Aug. 2, 2009.
GenBank Accession No. NM_006727 dated Oct. 18, 2009.
GenBank Accession No. NM_018930 dated Feb. 10, 2008.
GenBank Accession No. NM_080607 dated Sep. 3, 2009.
GenBank Accession No. NM_133445 dated Sep. 20, 2009.
GenBank Accession No. W34764 dated May 13, 1996.
Blute et al., "Use of Gleason score, prostate specific antigen, seminal vesicle and margin status to predict biochemical failure after radical prostatectomy," *J Urol*, 2001, 165:119-125.
Alberts et al., *Molecular Biology of the Cell*, 3rd Ed., 1994, p. 465.
Amling et al., "Long-term hazard of progression after radical prostatectomy for clinically localized prostate cancer continued risk of biochemical failure after 5 years," *J Urol.*, 2000, 164:101-105.
Amundadottir et al., "A common variant associated with prostate cancer in European and African populations," *Nat Genet.*, 2006, 38:652-658.
Amundson et al., "Integrating global gene expression and radiation survival parameters across the 60 cell lines of the National Cancer Institute Anticancer Drug Screen,"*Cancer Research*, 2008, 68(2):415-424.
International Preliminary Report on Patentability in PCT/US2007/079423 mailed Apr. 9, 2009, 6 pages.
International Search Report/Written Opinion in PCT/US2007/079423 mailed Feb. 27, 2008, 12 pages.
Ballman et al., "Faster cyclic loess: normalizing RNA arrays via linear models," *Bioinformatics*, 2004, 20:2778-2786.
Bergstralh et al., "Software for optimal matching in observational studies," *Epidemiology*, 1996, 7(3):331-332.
Best et al., "Molecular differentiation of high- and moderate-grade human prostate cancer by cDNA microarray analysis," *Diagn Mol Pathol.*, Jun. 2003, 12(2):63-70.
Bibikova et al., "Expression signatures that correlated with Gleason score and relapse in prostate cancer," *Genomics*, 2007, 89(6):666-672.
Bibikova et al., "Gene expression profiles in formalin-fixed, paraffin-embedded tissues obtained with a novel assay for microarray analysis," *Clin Chem.*, 2004, 50:2384-2386.
Bibikova et al., "Quantitative gene expression profiling in formalin-fixed, paraffin-embedded tissues using universal bead arrays," *Am J Pathol.*, 2004, 165:1799-1807.
Breiman, "Random Forests," *Machine Learning*, 2001, 45:5-32.
Bull et al., "Identification of potential diagnostic markers of prostate cancer and prostatic intraepithelial neoplasia using cDNA microarray," *Br J Cancer*, Jun. 1, 2001, 84(11):1512-1519.
Chen et al., "Hepsin and maspin are inversely expressed in laser capture microdissectioned prostate cancer," *J Urol.*, Apr. 2003, 169(4):1316-1319.
Cheville et al., "Gene panel model predictive of outcome in men at high-risk of system progression and death from prostate cancer after radical retropubic prostatectomy," *J. Clin Oncol.*, Aug. 20, 2008, 26(24):3930-3936.
U.S. Appl. No. 61/057,698, filed May 30, 2008, Klee et al.
Cologne and Shibata, "Optimal Case-Control Matching in Practice Epidemiology," 6(3):271-275, May 1995.
D'Amico et al., "Cancer-specific mortality after surgery or radiation for patients with clinically localized prostate cancer managed during the prostate-specific antigen era," *J Clin Oncol.*, 2003, 21:2163-2172.
D'Amico et al., "Determinants of prostate cancer-specific survival after radiation therapy for patients with clinically localized prostate cancer," *J Clin Oncol.*, 2002, 20:4567-4573.
De Marzo et al., "Pathological and molecular mechanisms of prostate carcinogenesis: implications for diagnosis, detection, prevention, and treatment," *J Cell Biochem.*, Feb. 15, 2004, 91(3):459-477.
Dhanasekaran et al., "Delineation of prognostic biomarkers in prostate cancer," *Nature*, 2001, 412:822-826.
Eder et al., "Genes differentially expressed in prostate cancer," *BJU Int.*, May 2004, 93(8):1151-1155.
Ernst et al., "Decrease and gain of gene expression are equally discriminatory markers for prostate carcinoma: a gene expression analysis on total and microdissected prostate tissue," *Am J Pathol.*, Jun. 2002, 160(6):2169-2180.
Office action from U.S. Appl. No. 12/474,879, dated Jan. 6, 2012, 15 pages.
Final Office Action from U.S. Appl. No. 12/442,685, dated Oct. 13, 2011, 8 pages.
Fan et al., "Concordance among gene-expression-based predictors for breast cancer," N Engl J Med., 2006, 355:560-569.
Foley et al., "Molecular pathology of prostate cancer: the key to identifying new biomarkers of disease," *Endocrine-Related Cancer*, 2004, 11:477-488.
GenBank Accession No. NM_000598, GI No. 62243067, dated Jun. 6, 2010, 5 pages.
GenBank Accession No. NM_000688, GI No. 40316942, dated Apr. 11, 2010, 5 pages.
GenBank Accession No. NM_001013398; GI No. 62243247, dated Jun. 6, 2010, 5 pages.
GenBank Accession No. NM_001039573, GI No. 221316683, dated Mar. 4, 2010, 5 pages.
GenBank Accession No. NM_001098533, GI No. 237858579, dated May 7, 2010, 5 pages.
GenBank Accession No. NM_001130851; GI No. 195927024, dated Mar. 5, 2010, 4 pages.
GenBank Accession No. NM_001136154 dated Jan. 8, 2012, 6 pages.
GenBank Accession No. NM_001136155 dated Jan. 8, 2012, 6 pages.
GenBank Accession No. NM_001143998, GI No. 221316675, dated Mar. 4, 2010, 5 pages.
GenBank Accession No. NM_001143999, GI No. 221316679, dated Mar. 5, 2010, 5 pages.
GenBank Accession No. NM_001144001, GI No. 221316686, dated Mar. 4, 2010, 5 pages.
GenBank Accession No. NM_001160367, GI No. 237858581, dated May 7, 2010, 5 pages.
GenBank Accession No. NM_003003, GI No. 221316681, dated Mar. 4, 2010, 5 pages.
GenBank Accession No. NM_003014; GI No. 170784837, dated Mar. 13, 2010, 5 pages.
GenBank Accession No. NM_003184; GI No. 115527086, dated Mar. 7, 2010, 7 pages.
GenBank Accession No. NM_004336; GI No. 211938448, dated Mar. 14, 2010, 6 pages.
GenBank Accession No. NM_004449 dated Jan. 8, 2012, 6 pages.
GenBank Accession No. NM_005192, GI No. 195927023, dated Mar. 4, 2010, 4 pages.
GenBank Accession No. NM_006265, GI No. 208879448, dated Apr. 11, 2010, 6 pages.
GenBank Accession No. NM_006819; GI No. 110225356, dated May 7, 2010, 5 pages.

GenBank Accession No. NM_012152; GI No. 183396778, dated Apr. 5, 2010, 5 pages.
GenBank Accession No. NM_014846; GI No. 120952850, dated Mar. 4, 2010, 6 pages.
GenBank Accession No. NM_016623; GI No. 42734437, dated Mar. 29, 2009, 4 pages.
GenBank Accession No. NM_031966 GI No. 34304372, dated Jun. 6, 2010, 5 pages.
GenBank Accession No. NM_032334; GI No. 223468686, dated Mar. 5, 2010, 3 pages.
GenBank Accession No. NM_052987, GI No. 237858574, dated May 7, 2010, 5 pages.
GenBank Accession No. NM_052988, GI No. 237858573, dated May 7, 2010, 5 pages.
GenBank Accession No. NM_080546; GI No. 112363101, dated May 7, 2010, 6 pages.
GenBank Accession No. NM_138455; GI No. 34147546, dated May 7, 2010, 3 pages.
GenBank Accession No. NM_182918 dated Jan. 8, 2012, 6 pages.
GenBank Accession No. NM_199166, GI No. 40316938, dated Apr. 11, 2010, 5 pages.
GenBank Accession No. NP_001058 dated Dec. 25, 2011, 9 pages.
Gleave et al., "Randomized comparative study of 3 versus 8-month neoadjuvant hormonal therapy before radical prostatectomy: biochemical and pathological effects," *J Urol.*, 2001, 166:500-507.
Glinsky et al., "Gene expression profiling predicts clinical outcome of prostate cancer," *J Clin Invest.*, 2004, 113:913-923.
Glinsky et al., "Microarray analysis identifies a death-from-cancer signature predicting therapy failure in patients with multiple types of cancer," *J Clin Invest.*, 2005, 115:1503-1521.
Gonzalgo and Isaacs, "Molecular pathways to prostate cancer," *J Urol.*, Dec. 2003, 170(6 Pt 1):2444-2452.
Greenbaum et al., "Comparing protein abundance and mRNA expression levels on a genomic scale," *Genome Biology*, 2003, 4(9):117.1-117.8.
Haiman et al., "Multiple regions within 8q24 independently affect risk for prostate cancer," *Nat Genet.*, 2007, 39:638-644.
Henrotin et al., "Type II collagen peptides for measuring cartilage degradation," *Biotheology*, 2004, 41(3-4): Abstract.
Holzbeierlein et al., "Gene expression analysis of human prostate carcinoma during hormonal therapy identifies androgen-responsive genes and mechanisms of therapy resistance," *Am. J. Pathol.*, Jan. 2004, 164(1):217-227.
Hughes et al., "Molecular pathology of prostate cancer," *J Clin Pathol.*, Jul. 2005, 58(7):673-684.
Jemal et al., "Cancer statistics," *CA Cancer J Clin.*, 2005, 55:10-30.
Karan et al., "Current status of the molecular genetics of human prostatic adenocarcinomas," *Int J Cancer*, Jan. 20, 2003, 103(3):285-293.
Karayi and Markham, "Molecular biology of prostate cancer," *Prostate Cancer Prostatic Dis.*, 2004, 7(1):6-20.
Kestin, "Potential survival advantage with early androgen deprivation for biochemical failure after external beam radiotherapy: the importance of accurately defining biochemical disease status," *Int J Rad Oncol Biol Phys.*, 2004, 60:453-62.
Kosari et al., "Identification of biomarkers for prostate cancer," *Clin. Cancer Res.*, 2008, 1734-1743.
Kube et al., "Optimization of laser capture microdissection and RNA amplification for gene expression profiling of prostate cancer," *BMC Mol. Biol.*, 2007, 8:25.
Lapointe et al., "Gene expression profiling identifies clinically relevant subtypes of prostate cancer," *Proc Natl Acad Sci USA*, 2004, 101:811-816.
Latulippe et al., "Comprehensive Gene Expression Analysis of Prostate Cancer Reveals Distinct Transcriptional Programs Associated with Metastatic Disease," *Cancer Res.*, 2002, 62:4499-4506.
Lawton et al., "Updated results of the phase III Radiation Therapy Oncology Group (RTOG) trial 85-31 evaluating the potential benefit of androgen suppression following standard radiation therapy for unfavorable prognosis carcinoma of the prostate," *Int J Rad Oncol Biol Phys.*, 2001, 49:937-946.
Luo et al., "Gene expression analysis of prostate cancers," *Mol Carcinog.*, Jan. 2002, 33(1):25-35.
Luo et al., "Human Prostate Cancer and Benign Prostatic Hyperplasia: Molecular Dissection by Gene Expression Profiling," *Cancer Res.*, 2001, 61:4683-4688.
Magee et al., "Expression Profiling Reveals Hepsin Overexpression in Prostate Cancer," *Cancer Res.*, 2001, 61:5692-5696.
Montironi et al., "Carcinoma of the prostate: inherited susceptibility, somatic gene defects and androgen receptors," *Virchows Arch.*, Jun. 2004, 444(6):503-508.
Moul et al., "Early versus delayed hormonal therapy for prostate specific antigen only recurrence of prostate cancer after radical prostatectomy," *J Urol.*, 2004, 171:1141-1147.
Moul, "Prostate specific antigen only progression of prostate cancer," *J Urol.*, 2000, 163:1632-42.
Nakagawa et al., A Tissue Biomarker Panel Predicting Systemic Progression after PSA Recurrence Post-Definitive Prostate Cancer Therapy, *PLos One*, 2008, 3(5):e2318, 14 pages.
Ohl et al., "Gene expression studies in prostate cancer tissue: which reference gene should be selected for normalization?," *J. Mol. Med.*, 2005, 83:1014-1024.
Parker et al., "High expression levels of survivin protein independently predict a poor outcome for patients who undergo surgery for clear cell renal cell carcinoma," *Cancer*, 2006, 107:37-45.
Pascal et al., "Correlation of mRNA and protein levels: Cell type-specific gene expression of cluster designation antigens in the prostate," *BMC Genomics*, 2008, 9:246 (13 pages).
Patel et al., "Preoperative PSA velocity is an independent prognostic factor for relapse after radical prostatectomy," *J Clin Oncol.*, 2005, 23:6157-6162.
Pereira et al, "Coagulation factor V and VIII/V ratio as predictors of outcome in paracetamol induced fulminant hepatic failure: relation to other prognostic indicators," Gut, 1992, 33:98-102.
Pienta et al., "The current state of preclinical prostate cancer animal models," *The Prostate*, 2008, 68:629-639.
Pilepich et al., "Phase III radiation therapy oncology group (RTOG) trial 86-10 of androgen deprivation adjuvant to definitive radiotherapy in locally advanced carcinoma of the prostate," *Int J Rad Oncol Biol Phys.*, 2001, 50:1243-1252.
Pinover et al., "Validation of a treatment policy for patients with prostate specific antigen failure after three-dimensional conformal prostate radiation therapy," *Cancer*, 2003, 97:1127-1133.
Porkka and Visakorpi, "Molecular mechanisms of prostate cancer," *Eur Urol.*, Jun. 2004, 45(6):683-691.
Porkka et al., "RAD21 and KIAA0196 at 8q24 are amplified and overexpressed in prostate cancer," *Genes Chromosomes Cancer*, 2007, 39:1-10.
Pound et al., "Natural history of progression after PSA elevation following radical prostatectomy," JAMA, 1999, 281:1591-1597.
Rhodes et al., "Large-scale meta-analysis of cancer microarray data identifies common transcriptional profiles of neoplastic transformation and progression," *Proc Natl Acad Sci USA*, 2004, 101:9309-9314.
Rhodes et al., "ONCOMINE: A Cancer Microarray Database and Integrated Data-Mining Platform," *Neoplasia*, 2004, 6:1-6.
Rubin and De Marzo, "Molecular genetics of human prostate cancer," *Mod Pathol*, Mar. 2004, 17(3):380-388.
Sandler et al., "Overall survival after prostate-specific-antigen-detected recurrence following conformal radiation therapy," *Int J Rad Oncol Biol Phys.*, 2000, 48:629-633.
Saramaki et al., "Amplification of EIF3S3 gene is associated with advanced stage in prostate cancer," *Am J Pathol.*, 2001, 159:2089-2094.
Sato et al., "Clinical significance of alterations of chromosome 8 in high-grade, advanced, nonmetastatic prostate carcinoma," *J Natl Cancer Inst.*, 1999, 91:1574-1580.
Savinainen et al., "Expression and copy number analysis of TRPS 1, EIF3S3 and MYC genes in breast and prostate cancer," *Br J Cancer*, 2004, 90:1041-1046.
Savinainen et al., "Over expression of EIF3S3 promotes cancer cell growth," *Prostate*, 2006, 66:1144-1150.
Schumacher et al., "A Common 8q24 Variant in Prostate and Breast Cancer from a Large Nested Case-Control Study," *Cancer Res.*, 2007, 67:2951-2956.

Severi et al., "The common variant rs1447295 on chromosome 8q24 and prostate cancer risk: results from an Australian population based case-control study," *Cancer Epidemiol Biomarkers Prev.*, 2007, 16:610-611.

Shipley et al., "Radiation therapy for clinically localized prostate cancer: a multi-institutional pooled analysis," *JAMA*, 1999, 281:1598-1604.

Singh et al., "Gene expression correlates of clinical prostate cancer behavior," *Cancer Cell*, 2002, 1:203-209.

Stamey et al., "Molecular genetic profiling of Gleason grade 4/5 prostate cancers compared to benign prostatichyperplasia," *J Urol.*, Dec. 2001, 166(6):2171-2177.

Stephenson et al., "Integration of gene expression profiling and clinical variables to predict prostate carcinoma recurrence after radical prostatectomy," *Cancer*, Jul. 15, 2005, 104(2):290-298.

Subramanian et al., "Gene set enrichment analysis: A knowledge-based approach for interpreting genome-wide expression profiles," *Proc Natl Acad Sci USA*, 2005, 102:15545-15550.

Supplemental Table 3 of U.S. Appl. No. 61/057,698, filed May 30, 2008.

Supplemental Table 4 of U.S. Appl. No. 61/057,698, filed May 30, 2008.

Supplemental Table 5 of U.S. Appl. No. 61/057,698, filed May 30, 2008.

Supplemental Table 6 of U.S. Appl. No. 61/057,698, filed May 30, 2008.

Supplemental Tables 1 and 2 of U.S. Appl. No. 61/057,698, filed May 30, 2008.

Tockman et al., "Considerations in bringing a cancer biomarker to clinical application," *Cancer Research*, 1992, 52:2711s-2718s.

Tollefson et al., "Stratification of Patient Risk Based on Prostate-Specific Antigen Doubling Time After Radical Retropubic Prostatectomy," *Mayo Clin Proc.*, 2007, 82:422-427.

Tomlins et al., "Integrative molecular concept modeling of prostate cancer progression," *Nat Genet.*, 2007, 39:41-51.

Tomlins et al., "Recurrent Fusion of TMPRSS2 and ETS Transcription Factor Genes in Prostate Cancer," *Science*, 2005, 310(5748):644-648.

Tomlins et al., "TMPRSS2:ETV4 Gene Fusions Define a Third Molecular Subtype of Prostate Cancer," *Cancer Res.*, 2006, 66:3396-3400.

Tricoli et al., "Detection of prostate cancer and predicting progression: current and future diagnostic markers," *Clinical Cancer Research*, Jun. 15, 2004, 10:3943-3953.

Tsuchiya et al., "Clinical significance of alterations of chromosome 8 detected by fluorescence *in situ* hybridization analysis in pathologic organ-confined prostate cancer," *Genes Chromosomes Cancer*, 2002, 34:363-371.

Tsuchiya et al., "Mapping and gene expression profile of the minimally overrepresented 8q24 region in prostate cancer," *Am J Pathol.*, 2002, 160:1799-1806.

Varambally et al., "Integrative Genomic and Proteomic Analysis of Prostate Cancer Reveals Signatures of Metastatic Progression," *Cancer Cell*, Nov. 2005, 8(5):393-406.

Visakorpi, "The molecular genetics of prostate cancer," *Urology*, Dec. 29, 2003, 62 Suppl 1:19-35.

Wang et al., "Two common chromosome 8q24 variants are associated with increased risk for prostate cancer," *Cancer Res.*, 2007, 67:2944-2950.

Watson and Schalken, "Future opportunities for the diagnosis and treatment of prostate cancer," *Prostate Cancer Prostatic Dis.*, 2004, 7:S8-S13.

Welsh et al., "Analysis of Gene Expression Identifies Candidate Markers and Pharmacological Targets in Prostate Cancer," *Cancer Res.*, 2001, 61:5974-5978.

Yeager et al., "Genome-wide association study of prostate cancer identifies a second risk locus at 8q24," *Nat Genet.*, 2007, 39:645-649.

Yu et al., "Gene expression alterations in prostate cancer predicting tumor aggression and preceding development of malignancy," *J Clin Oncol.*, Jul. 15, 2004, 22(14):2790-2799.

Zelefsky et al., "Neoadjuvant hormonal therapy improves the therapeutic ratio in patients with bulky prostatic cancer treated with three-dimensional conformal radiation therapy," *Int J Radiat Oncol Biol Phys.*, 1994, 29:755-761.

\* cited by examiner

ID

SEQUENCE LISTING

```
<160> NUMBER OF SEQ ID NOS: 14

<210> SEQ ID NO 1
<211> LENGTH: 22
<212> TYPE: DNA
<213> ORGANISM: Homo sapiens

<400> SEQUENCE: 1
catggcctcc aaggagtaag ac                                              22

<210> SEQ ID NO 2
<211> LENGTH: 23
<212> TYPE: DNA
<213> ORGANISM: Homo sapiens

<400> SEQUENCE: 2
tctcttcctc ttgtgctctt gct                                             23

<210> SEQ ID NO 3
<211> LENGTH: 18
<212> TYPE: DNA
<213> ORGANISM: Homo sapiens

<400> SEQUENCE: 3
gctgctcgct gggtcttg                                                   18

<210> SEQ ID NO 4
<211> LENGTH: 23
<212> TYPE: DNA
<213> ORGANISM: Homo sapiens

<400> SEQUENCE: 4
ggagcagatt gtgacagacc att                                             23

<210> SEQ ID NO 5
<211> LENGTH: 20
<212> TYPE: DNA
<213> ORGANISM: Homo sapiens
```

```
<400> SEQUENCE: 5
gctgccacaa tcagaaatca                                              20

<210> SEQ ID NO 6
<211> LENGTH: 20
<212> TYPE: DNA
<213> ORGANISM: Homo sapiens

<400> SEQUENCE: 6
tcgcgactca aaggaaaact                                              20

<210> SEQ ID NO 7
<211> LENGTH: 20
<212> TYPE: DNA
<213> ORGANISM: Homo sapiens

<400> SEQUENCE: 7
tggctgcctc tgagtctgaa                                              20

<210> SEQ ID NO 8
<211> LENGTH: 24
<212> TYPE: DNA
<213> ORGANISM: Homo sapiens

<400> SEQUENCE: 8
agtcttctgc aatccagtcc tctt                                         24

<210> SEQ ID NO 9
<211> LENGTH: 25
<212> TYPE: DNA
<213> ORGANISM: Homo sapiens

<400> SEQUENCE: 9
gaacaggata gttctccctt aagca                                        25

<210> SEQ ID NO 10
<211> LENGTH: 23
<212> TYPE: DNA
<213> ORGANISM: Homo sapiens

<400> SEQUENCE: 10
caagggcagg acatgtacct aac                                          23

<210> SEQ ID NO 11
<211> LENGTH: 20
<212> TYPE: DNA
<213> ORGANISM: Homo sapiens

<400> SEQUENCE: 11
tgtttttgct ttgcatttgg                                              20

<210> SEQ ID NO 12
<211> LENGTH: 22
<212> TYPE: DNA
<213> ORGANISM: Homo sapiens

<400> SEQUENCE: 12
tccccattta ctcatggttt tt                                           22

<210> SEQ ID NO 13
<211> LENGTH: 20
<212> TYPE: DNA
<213> ORGANISM: Homo sapiens
```

```
<400> SEQUENCE: 13
gcagatcccc actgtcctac                                          20

<210> SEQ ID NO 14
<211> LENGTH: 20
<212> TYPE: DNA
<213> ORGANISM: Homo sapiens

<400> SEQUENCE: 14 ccactttcc ttcccaatga                                           20
```

PREDICTING CANCER OUTCOME

CROSS-REFERENCE TO RELATED APPLICATION

This application is a National Stage application under 35 U.S.C. 371 and claims benefit under 35 U.S.C. 119(a) of International Application No. PCT/US2007/083504 having an International Filing Date of Nov. 2, 2007, which claims the benefit of U.S. Provisional Application Ser. No. 60/856,536, filed Nov. 2, 2006, the contents of which are incorporated herein by reference.

BACKGROUND

1. Technical Field

This document relates to methods and materials involved in assessing prostate cancer in male mammals. For example, this document provides methods and materials for determining whether a mammal having prostate cancer is susceptible to a good or poor outcome.

2. Background Information

Two of the major decision-making points related to therapy for patients with prostate cancer are at the time of biopsy and after radical prostatectomy. Positive biopsies contain a small portion of the tumor for diagnosis of aggressiveness. Based on morphological parameters such as Gleason score, patients are given three choices. In the case of benign or less aggressive disease, the choices are either watchful waiting or surgery. Immediate surgery is recommended in intermediate situations to prevent further advance. Radiation or hormonal therapies are recommended if the cancer has metastasized and surgery would not help. After surgery, when the bulk of the tumor is available for more thorough diagnosis, decisions still have to be made concerning additional therapies such as radiation or hormonal treatment that could depend on the aggressiveness of the disease. Determining disease aggressiveness is important for clinical decisions towards the management of prostate cancer patients.

SUMMARY

This document provides methods and materials related to assessing prostate cancer in mammals (e.g., human males). For example, this document provides methods and materials for determining whether or not a mammal has an aggressive form of prostate cancer.

Gleason grade, stage, ploidy, and margin status are major descriptors of prostate cancer aggressiveness and are thought to be important in determining cancer management. However, these clinicopathological parameters have significant drawbacks. For example, Gleason grading is heavily dependent upon the visual interpretation (Gleason, *Hum. Pathol.*, 23:273-279 (1992); Gleason and Vacurg (1977) Histologic grading and clinical staging of prostatic carcinoma. In *Urologic pathology: the prostate* (Tannenbaum M., ed.) Lea & Febiger, Philadelphia, Pa. 171-213). In addition, the level of resolution of this grading system appears to be too coarse as it is dependent on architectural pattern rather than cytologic changes. This concern is supported by the high level of uncertainty regarding the clinical outcome of patients with intermediate Gleason grades. Identifying cancer patients who have a poor prognosis can allow such patients, who are at risk for progression, to be offered more aggressive therapy earlier. In addition, identifying cancer patients who do not have a poor prognosis can avoid unnecessary treatment and suffering.

This document is based in part on the discovery of nucleic acids, referred to herein as aggressive prostate cancer biomarkers, having variant over-expression in aggressive tumors. Such nucleic acids, as well as polypeptides encoded by such nucleic acids, can be analyzed to assess prostate cancer in mammals. Analysis of the nucleic acids, or polypeptides encoded by the nucleic acids, can allow prostate cancer to be assessed in mammals based on an elevated level of one or more of the nucleic acids or polypeptides in a biological sample (e.g., a prostate biopsy specimen) from the mammal. The levels of multiple nucleic acids or polypeptides can be detected simultaneously using nucleic acid or polypeptide arrays.

In one aspect, a method for assessing prostate cancer is provided. The method comprises, or consists essentially of, determining whether or not a mammal having prostate cancer comprises an elevated level of expression of a KHDRBS3, NRP1, COL10A1, C20orf102, SSTR1, RRM2, F5, HSPC150, CDC2, TOP2A, SERPINI1, TDO2, GRIN3A, COL2A1 or PCDHB10 nucleic acid, or a polypeptide encoded by the nucleic acid, where the presence of the elevated level indicates that the mammal is susceptible to a poor outcome. The method can comprise determining whether or not a mammal having prostate cancer comprises an elevated level of an NRP1, SSTR1, KHDRBS3, or RRM2 nucleic acid, or a polypeptide encoded by the NRP1, SSTR1, KHDRBS3, or RRM2 nucleic acid. The mammal can be a human. The level can be determined in prostate tissue. The level can be determined using PCR or in situ hybridization. The level can be determined using immunohistochemistry. The poor outcome can comprise systemic progression within five years of prostatectomy.

In another aspect, a method for assessing prostate cancer is provided. The method comprises, or consists essentially of, (a) determining whether or not a mammal has an aggressive prostate cancer profile, and (b) classifying the mammal as susceptible to a poor outcome if the mammal has the aggressive prostate cancer profile and classifying the mammal as not susceptible to a poor outcome if the mammal does not have the aggressive prostate cancer profile. The mammal can be a human. The aggressive prostate cancer profile can be determined in prostate tissue. The aggressive prostate cancer profile can be determined using PCR or a nucleic acid array. The aggressive prostate cancer profile can be determined using immunohistochemistry or an array for detecting polypeptides. The poor outcome can comprise systemic progression within five years of prostatectomy.

In another aspect, this document provides a method for assessing prostate cancer. The method comprises, or consists essentially of, determining whether or not a mammal having prostate cancer comprises a reduced level of expression of a CDH10 nucleic acid, or a polypeptide encoded by the nucleic acid, wherein the presence of the reduced level indicates that the mammal is susceptible to a poor outcome. The mammal can be a human. The level can be determined in prostate tissue. The level can be determined using PCR or in situ hybridization. The level can be determined using immunohistochemistry. The poor outcome can comprise systemic progression within five years of prostatectomy.

In another aspect, this document provides a method for assessing prostate cancer. The method comprises, or consists essentially of, determining whether or not a mammal having prostate cancer comprises an elevated level of expression of a ST6GALNAC5, DIRAS2, or BIRC5 nucleic acid, or a polypeptide encoded by the nucleic acid, wherein the presence of the elevated level indicates that the mammal is susceptible to a poor outcome. The mammal can be a human. The level can be determined in prostate tissue. The level can be determined using PCR or in situ hybridization. The level can be determined using immunohistochemistry. The poor outcome can comprise systemic progression within five years of prostatectomy.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
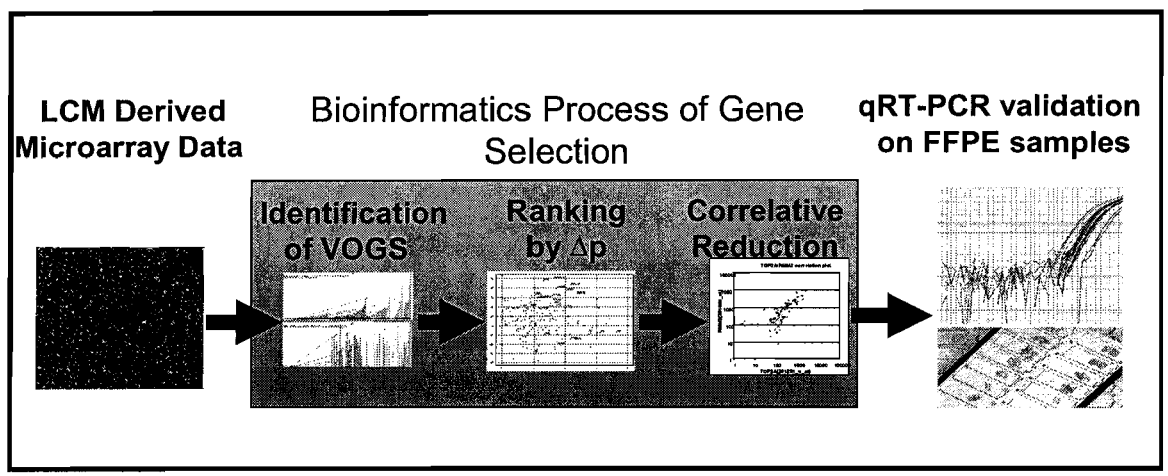
FIG. 1 is an illustration of the biomarker discovery and validation process.

This document provides methods and materials related to assessing prostate cancer in mammals. For example, this document provides methods and materials for determining whether or not a biological sample (e.g., prostate tissue sample) from a mammal (e.g., a male human) contains an elevated level of one or more than one aggressive prostate cancer biomarker. An aggressive prostate cancer biomarker can be a KHDRBS3, NRP1, COL10A1, C20orf102, SSTR1, RRM2, F5, HSPC150, CDC2, TOP2A, SERPINI1, TDO2, GRIN3A, COL2A1, PCDHB10, ST6GALNAC5, DIRAS2, or BIRC5 nucleic acid or polypeptide, or a nucleic acid or polypeptide listed in Table 2 or Table 3. As described herein, if the level of an aggressive prostate cancer biomarker in a sample from a mammal is elevated, then the mammal can be classified as being susceptible to a poor outcome. If the level of an aggressive prostate cancer biomarker in a sample from a mammal is not elevated, then the mammal can be classified as not being susceptible to a poor outcome. In some cases, a reduced or low level of expression of a cancer biomarker (e.g., CDH10) can indicate the presence of aggressive prostate cancer. As described herein, an elevated level of CDH10 can indicate the presence of prostate cancer, and a reduced level of CDH10 can indicate the presence of aggressive prostate cancer.

In some cases, a mammal can be classified as being susceptible to a poor outcome if it is determined that a sample (e.g., prostate tissue) from the mammal has an aggressive prostate cancer profile. For the purpose of this document, the term "aggressive prostate cancer profile" as used herein refers to a nucleic acid or polypeptide profile in a sample where one or more than one (e.g., 1, 2, 3, 4, 5, 6, 7, 8, 9, 10, 11, 12, 13, 14, 15, 16, 17, 18, or more) of a KHDRBS3, NRP1, COL10A1, C20orf102, SSTR1, RRM2, F5, HSPC150, CDC2, TOP2A, SERPINI1, TDO2, GRIN3A, COL2A1, PCDHB10, ST6GALNAC5, DIRAS2, or BIRC5 nucleic acid or polypeptide, or fragment thereof, or a nucleic acid or polypeptide listed in Table 2 or Table 3, or fragment thereof, is present at an elevated level. In some cases, the aggressive prostate cancer profile can be a profile in a sample where a majority of a KHDRBS3, NRP1, COL10A1, C20orf102, SSTR1, RRM2, F5, HSPC150, CDC2, TOP2A, SERPINI1, TDO2, GRIN3A, COL2A1, PCDHB10, ST6GALNAC5, DIRAS2, or BIRC5 nucleic acid or polypeptide, and the nucleic acids or polypeptides listed in Table 2 and Table 3, is present at an elevated level.

The term "aggressive" as used herein refers to the invasive and metastatic activity of a cancer. For example, an aggressive prostate cancer is more invasive and metastatic than a less aggressive prostate cancer. Aggressive cancers can produce adverse changes in a mammal's overall health to a greater extent than if that cancer were not aggressive. A mammal with an aggressive prostate cancer can, for example, experience bladder obstruction problems to a greater extent than if that prostate cancer were not aggressive. Other adverse changes in overall health include, without limitation, edema, mineral and vitamin deficiencies, increased risk of infection, loss of appetite, depression, enlargement of organs such as lymph nodes, and pain associated with metastasis. Aggressive cancers can increase mortality to a greater extent than less aggressive cancers. For example, aggressive prostate cancer can cause a poor outcome such as systemic progression within five years of prostatectomy.

To assess the aggressiveness of prostate cancer in a mammal, the level of one or more than one aggressive prostate cancer biomarker can be analyzed in a sample from the mammal. The level of an aggressive prostate cancer biomarker can be determined by measuring any aggressive prostate cancer biomarker including, without limitation, native, truncated, and mutant aggressive prostate cancer biomarkers, as well as any fragments thereof. Examples of aggressive prostate cancer biomarkers include, without limitation, human KHDRBS3 (GenBank Accession No. NM_006558, NP_006549), NRP1 (GenBank Accession No. NM_003873.3, NP_003864), COL10A1 (GenBank Accession No. NM_000493, NP_000484.2), C20orf102 (GenBank Accession No. NM_080607, NP_542174.1), SSTR1 (GenBank Accession No. NM_001049, NP_001040.1), RRM2 (GenBank Accession No. NM_001034, NP_001025.1), F5 (GenBank Accession No. NM_000130, NP_000121.2), CDC2 (GenBank Accession No. NM_001786, NP_001777.1), TOP2A (GenBank Accession No. NM_001067, NP_001058.2), CDH10 (GenBank Accession No. NM_006727, NP_006718.2), SERPINI1 (GenBank Accession No. NM_005025.2, NP_005016.1), TDO2 (GenBank Accession No. NM_005651.1, NP_005642.1), GRIN3A (GenBank Accession No. NM_133445, NP_597702.1), COL2A1 (GenBank Accession No. NM_001844, NP_001835.2), PCDHB10 (GenBank Accession No. NM_018930, NP_061753.1), ST6GALNAC5 (GenBank Accession Nos. AA462934, AB028840, AB030836, AI851940, AK034387, AK038434, AK042683, and BC055737), DIRAS2 (GenBank Accession Nos. AA920095, AI414999, AI425960, AK019341, AK019342, AK041534, AK136096, AK136101, BC086799, BF449664, and BM114282), or BIRC5 (GenBank Accession Nos. AB036741, AF077349, AF077351, AF115517, AI413910, AK018022, AK038229, AK142768, AL591433, BC004702, BG063957, BG077309, BY023910, CN724527, and W34764) nucleic acids and polypeptides.

The term "elevated level" as used herein with respect to the level of an aggressive prostate cancer biomarker is any level that is greater than a reference level for that aggressive prostate cancer biomarker. The term "reference level" as used herein with respect to an aggressive prostate cancer biomarker is the level of that aggressive prostate cancer biomarker typically expressed by mammals free of aggressive prostate cancer. For example, a reference level of an aggressive prostate cancer biomarker can be the average level of that aggressive prostate cancer biomarker that is present in samples obtained from a random sampling of 50 males with prostate cancer who did not have systemic progression for at least seven years after having a prostatectomy. In some cases, a reference level can be the average level of an aggressive prostate cancer biomarker that is present in samples obtained from a random sampling of 50 males with a prostate cancer of Gleason score 7 who did not have systemic progression for at least seven years after having a prostatectomy.

It will be appreciated that levels from comparable samples are used when determining whether or not a particular level is an elevated level. For example, the average level of an aggressive prostate cancer biomarker present in bulk prostate tissue from a random sampling of mammals may be X units/g of prostate tissue, while the average level of the aggressive prostate cancer biomarker present in isolated prostate epithelial cells may be Y units/number of prostate cells. In this case, the reference level for the aggressive prostate cancer biomarker in bulk prostate tissue would be X units/g of prostate tissue, and the reference level for the aggressive prostate cancer biomarker in isolated prostate epithelial cells would be Y units/number of prostate cells. Thus, when determining whether or not the level of an aggressive prostate cancer biomarker in bulk prostate tissue is elevated, the measured level would be compared to the reference level for the aggressive prostate cancer biomarker in bulk prostate tissue. In some cases, the reference level of an aggressive prostate cancer biomarker can be a ratio of an expression value of the biomarker in a sample to an expression value of a control nucleic acid or polypeptide in the sample. A control nucleic acid or polypeptide can be any polypeptide or nucleic acid that has a minimal variation in expression level across various samples of the type for which the nucleic acid or polypeptide serves as a control. For example, GAPDH, HPRT, NDUFA7, and RPS16 nucleic acids or polypeptides can be used as control nucleic acids or polypeptides, respectively, in prostate samples.

An elevated level of an aggressive prostate cancer biomarker can be any level provided that the level is greater than a corresponding reference level for that aggressive prostate cancer biomarker. For example, an elevated level of an aggressive prostate cancer biomarker can be 1.1, 1.2, 1.3, 1.4, 1.5, 1.6, 1.7, 1.8, 1.9, 2.0, 2.2, 2.4, 2.6, 2.8, 3, 3.2, 3.4, 3.6, 3.8, 4, 4.2, 4.4, 4.6, 4.8, 5, 6, 7, 8, 9, 10, 15, 20, or more times greater than the reference level for that aggressive prostate cancer biomarker. In addition, a reference level can be any amount. For example, a reference level for an aggressive prostate cancer biomarker can be zero. In this case, any level of the aggressive prostate cancer biomarker greater than zero would be an elevated level.

Any appropriate method can be used to determine the level of an aggressive prostate cancer biomarker present within a sample. For example, quantitative PCR, in situ hybridization, or microarray technology can be used to determine the level of an aggressive prostate cancer biomarker in a sample. In some cases, the level of an aggressive prostate cancer biomarker can be determined using polypeptide detection methods such as immunochemistry techniques. For example, antibodies specific for an aggressive prostate cancer biomarker can be used to determine the polypeptide level of the aggressive prostate cancer biomarker in a sample.

Any appropriate type of sample can be used to evaluate the level of an aggressive prostate cancer biomarker including, without limitation, prostate tissue, seminal vesicle tissue, lymphatic tissue, serum, urine, and other body fluids. In addition, any appropriate method can be used to obtain a sample. For example, a prostate tissue sample can be obtained by a tissue biopsy or following surgical resection. Once obtained, a sample can be processed prior to measuring the level of an aggressive prostate cancer biomarker. For example, a prostate tissue sample can be processed to extract RNA from the sample. Once obtained, the RNA can be evaluated to determine the level of one or more than one aggressive prostate cancer biomarker present. In some embodiments, nucleic acids present within a sample can be amplified (e.g., linearly amplified) prior to determining the level of one or more than one aggressive prostate cancer biomarker (e.g., using array technology). In another example, a prostate tissue sample can be frozen, and sections of the frozen tissue sample can be prepared on glass slides. The frozen tissue sections can be stored (e.g., at −80° C.) prior to analysis, or they can be analyzed immediately (e.g., by immunohistochemistry with an antibody specific for an aggressive prostate cancer biomarker). In some cases, the level of a KHDRBS3, NRP1, COL10A1, C20orf102, SSTR1, RRM2, F5, HSPC150, CDC2, TOP2A, SERPINI1, TDO2, GRIN3A, COL2A1, PCDHB10, ST6GALNAC5, DIRAS2, or BIRC5 nucleic acid or polypeptide, or a nucleic acid or polypeptide listed in Table 2, or any combination thereof, can be evaluated in a prostate tissue sample obtained following a prostatectomy procedure. In some cases, the level of one or more than one nucleic acid or polypeptide listed in Table 3 can be evaluated in a prostate tissue sample obtained by a tissue biopsy.

Once the level of an aggressive prostate cancer biomarker in a sample from a mammal is determined, then the level can be compared to a reference level for that aggressive prostate cancer biomarker and used to evaluate the susceptibility of the mammal to a poor outcome. A level of one or more than one aggressive prostate cancer biomarker in a sample from a mammal that is higher than the corresponding one or more than one reference level can indicate that the mammal is susceptible to a poor outcome. In contrast, a level of one or more than one aggressive prostate cancer biomarker in a sample from a mammal that is equal to or lower than the corresponding one or more than one reference level can indicate that the mammal is not susceptible to a poor outcome.

In some cases, the aggressiveness and outcome of prostate cancer can be assessed based on the numbers and/or levels of aggressive prostate cancer biomarkers in a sample from a mammal. The greater the number of aggressive prostate cancer biomarkers present at an elevated level in a sample from the mammal, the more aggressive is the prostate cancer in the mammal, and the more susceptible is the mammal to a poor outcome. In addition, the greater the differences between the levels of the aggressive prostate cancer biomarkers in a sample from a mammal and the corresponding reference levels, the more likely the prostate cancer is to progress in the mammal.

In some cases, the levels of aggressive prostate cancer biomarkers in a sample can be used in combination with one or more other factors to determine whether or not a mammal having prostate cancer is susceptible to a poor outcome. For example, levels of aggressive prostate cancer biomarkers in a sample from a mammal having prostate cancer can be used in combination with the clinical stage, the serum PSA level, and/or the Gleason score of the prostate cancer to determine whether or not the mammal is likely to have to a poor outcome. Additional information about the mammal, such as information concerning genetic predisposition to develop cancer, SNPs, chromosomal abnormalities, gene amplifications or deletions, and/or post translational modifications, can also be used in combination with the level of one or more aggressive prostate cancer biomarkers to assess the aggressiveness and outcome of prostate cancer. In some cases, the level of one or more aggressive prostate cancer biomarkers in a sample from a mammal can be used in combination with the Gleason score, preoperative PSA, seminal vesicle invasion, and margin status to determine whether or not the mammal is susceptible to a poor outcome (Blute et al., *J. Urol.*, 165(1): 119-25 (2001)).

This document also provides methods and materials to assist medical or research professionals in determining whether or not a mammal having prostate cancer is susceptible to a poor outcome. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining the level of one or more than one aggressive prostate cancer biomarker in a sample, and (2) communicating information about that level to that professional.

Any method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

This document also provides nucleic acid arrays. The arrays provided herein can be two-dimensional arrays, and can contain at least two different nucleic acid molecules (e.g., at least three, at least five, at least ten, at least 20, at least 30, at least 40, at least 50, or at least 60 different nucleic acid molecules). Each nucleic acid molecule can have any length. For example, each nucleic acid molecule can be between 10 and 250 nucleotides (e.g., between 12 and 200, 14 and 175, 15 and 150, 16 and 125, 18 and 100, 20 and 75, or 25 and 50 nucleotides) in length. In some cases, an array can contain one or more cDNA molecules encoding, for example, partial or entire polypeptides. In addition, each nucleic acid molecule can have any sequence. For example, the nucleic acid molecules of the arrays provided herein can contain sequences that are present within aggressive prostate cancer biomarkers.

In some cases, at least 25% (e.g., at least 30%, at least 40%, at least 50%, at least 60%, at least 75%, at least 80%, at least 90%, at least 95%, or 100%) of the nucleic acid molecules of an array provided herein contain a sequence that is (1) at least 10 nucleotides (e.g., at least 11, 12, 13, 14, 15, 16, 17, 18, 19, 20, 25, or more nucleotides) in length and (2) at least about 95 percent (e.g., at least about 96, 97, 98, 99, or 100) percent identical, over that length, to a sequence present within an aggressive prostate cancer biomarker. For example, an array can contain 60 nucleic acid molecules located in known positions, where each of the 60 nucleic acid molecules is 100 nucleotides in length while containing a sequence that is (1) 90 nucleotides is length, and (2) 100 percent identical, over that 90 nucleotide length, to a sequence of an aggressive prostate cancer biomarker. A nucleic acid molecule of an array provided herein can contain a sequence present within an aggressive prostate cancer biomarker where that sequence contains one or more (e.g., one, two, three, four, or more) mismatches.

The nucleic acid arrays provided herein can contain nucleic acid molecules attached to any suitable surface (e.g., plastic, nylon, or glass). In addition, any appropriate method can be used to make a nucleic acid array. For example, spotting techniques and in situ synthesis techniques can be used to make nucleic acid arrays. Further, the methods disclosed in U.S. Pat. Nos. 5,744,305 and 5,143,854 can be used to make nucleic acid arrays.

This document also provides arrays for detecting polypeptides. The arrays provided herein can be two-dimensional arrays, and can contain at least two different polypeptides capable of detecting polypeptides, such as antibodies (e.g., at least three, at least five, at least ten, at least 20, at least 30, at least 40, at least 50, or at least 60 different polypeptides capable of detecting polypeptides). The arrays provided herein also can contain multiple copies of each of many different polypeptides. In addition, the arrays for detecting polypeptides provided herein can contain polypeptides attached to any suitable surface (e.g., plastic, nylon, or glass).

A polypeptide capable of detecting a polypeptide can be naturally occurring, recombinant, or synthetic. The polypeptides immobilized on an array also can be antibodies. An antibody can be, without limitation, a polyclonal, monoclonal, human, humanized, chimeric, or single-chain antibody, or an antibody fragment having binding activity, such as a Fab fragment, F(ab') fragment, Fd fragment, fragment produced by a Fab expression library, fragment comprising a VL or VH domain, or epitope binding fragment of any of the above. An antibody can be of any type, (e.g., IgG, IgM, IgD, IgA or IgY), class (e.g., IgG1, IgG4, or IgA2), or subclass. In addition, an antibody can be from any animal including birds and mammals. For example, an antibody can be a mouse, chicken, human, rabbit, sheep, or goat antibody. Such an antibody can be capable of binding specifically to an aggressive prostate cancer biomarker. The polypeptides immobilized on the array can be members of a family such as a receptor family, protease family, or an enzyme family.

Antibodies can be generated and purified using any suitable methods known in the art. For example, monoclonal antibodies can be prepared using hybridoma, recombinant, or phage display technology, or a combination of such techniques. In some cases, antibody fragments can be produced synthetically or recombinantly from a nucleic acid encoding the partial antibody sequence. In some cases, an antibody fragment can be enzymatically or chemically produced by fragmentation of an intact antibody. In addition, numerous antibodies are available commercially. An antibody directed against an aggressive prostate cancer biomarker can bind the polypeptide at an affinity of at least $10^4$ mol$^{-1}$ (e.g., at least $10^5$, $10^6$, $10^7$, $10^8$, $10^9$, $10^{10}$, $10^{11}$, or $10^{12}$ mol$^{-1}$).

Any method can be used to make an array for detecting polypeptides. For example, methods disclosed in U.S. Pat. No. 6,630,358 can be used to make arrays for detecting polypeptides. Arrays for detecting polypeptides can also be obtained commercially, such as from Panomics, Redwood City, Calif.

The invention will be further described in the following examples, which do not limit the scope of the invention described in the claims.

EXAMPLES

Example 1

Gene Expression Profiling

Gene expression was profiled in cancerous and non-cancerous prostate epithelial cells using microarray technology. The cells were collected from 101 frozen tissue samples using laser capture microdissection. Benign epithelial cells adjacent to tumor tissue were collected from 19 tissue samples (cases). Cells were also collected from 10 benign prostatic hyperplasia (BPH) cases, 5 prostatic intraepithelial neoplasia (PIN) cases, 30 cases with only Gleason pattern 3 (Gleason score 6), 20 cases with only Gleason pattern 4 (Gleason score 8), and 10 cases with only Gleason pattern 5 (Gleason score 10). In addition, prostatic adenocarcinoma cells were collected from 7 cases with lymph node metastases. Total RNA was extracted from cells of each type collected. Each RNA sample was linearly amplified, labeled, and hybridized to a U133 Plus 2.0 array (Affymetrix, Santa Clara, Calif.). The arrays were washed, stained, and scanned. The gene expression data were analyzed using dChip and GCOS 6.0 software. In analyzing the data with dChip, invariant set normalization and PM/MM Model Based Expression values were generated.

Example 2

Biomarker Discovery

The gene expression data generated as described in Example 1 were analyzed using bioinformatics. The bioinformatics analysis was designed to account for the heterogeneity of prostate cancer better than other methods that require more consistent differential expression of nucleic acids in tumor samples. The analysis included three steps (FIG. 1). In the first step, probesets were identified that had significantly higher expression levels in a subset of tumors than in non-neoplastic tissues. Genes corresponding to these probesets were named variably overexpressed genes, or VOGs. In the second step, genes associated with prostate cancer outcome were identified by selecting probesets that were over-expressed in a higher percentage of aggressive tumors than non-aggressive tumors. Gleason pattern was used as a surrogate measure of aggressiveness. In the third step, genes that had similar expression patterns across tumor samples were grouped to minimize overlap of prognostic information and reduce the number of genes to validate on independent patient samples.

Figure 2:
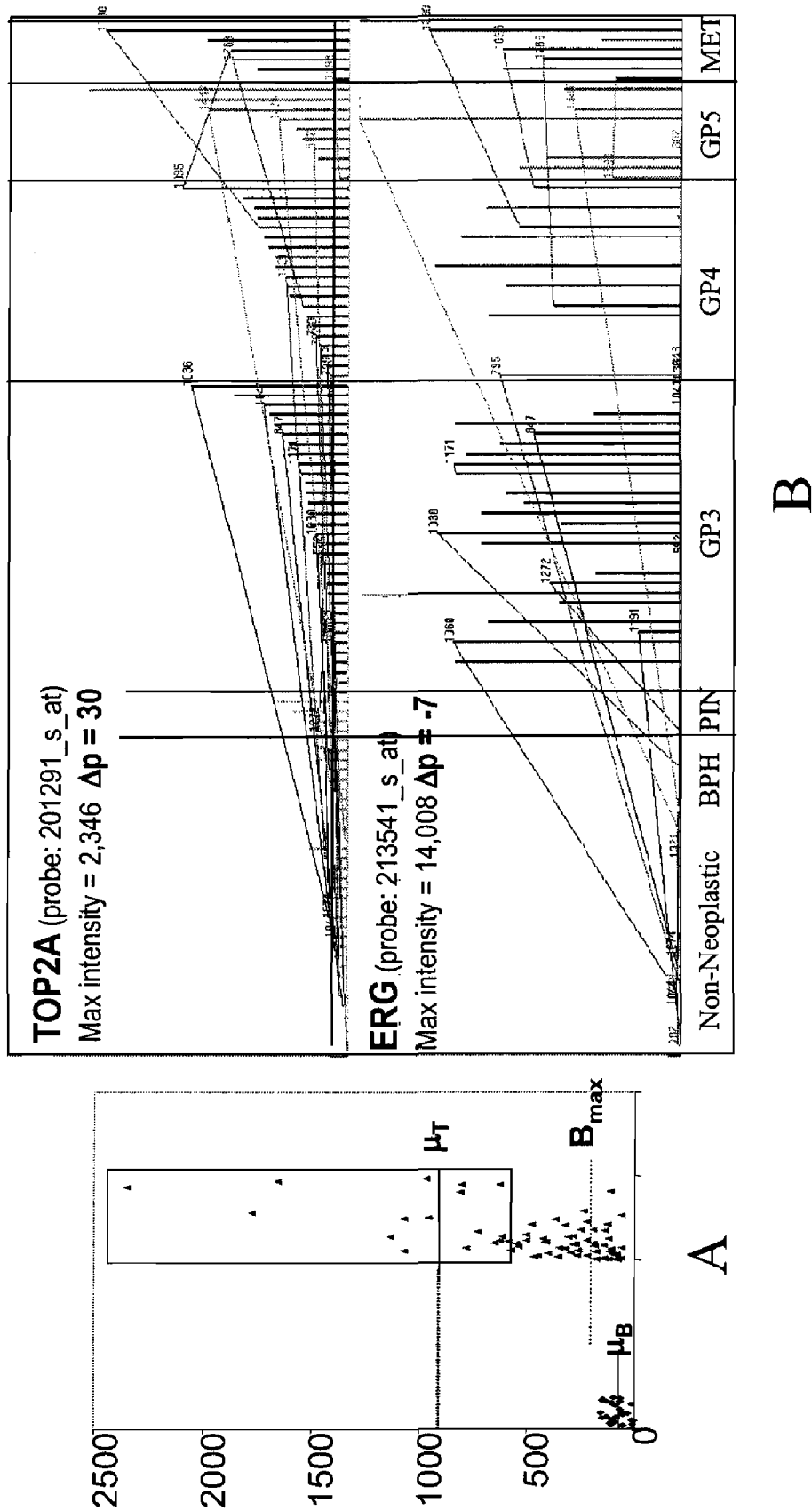
FIG. 2A depicts the algorithm used to identify over-expressed probesets by the Variably Over-expressed Genes (VOG) approach. $B_{max}$ and $\mu_B$ represent the maximum and mean expression levels, respectively, in non-neoplastic samples, respectively, and $\mu_T$, represents the mean expression in the tumor samples that over-express the gene.
FIG. 2B contains graphs plotting expression values of probesets corresponding to TOP2A and ERG nucleic acids in samples of cancerous and non-cancerous prostate epithelial cells. Lines connecting expression values in pairs of samples illustrate selection of the probesets by VOG. The samples represent benign, prostatic intraepithelial neoplasia (PIN) GP3, GP4, GP5, and metastasis samples. The Δp parameter is the difference between the percentages of highly aggressive and less aggressive prostate cancer cases that overexpress the gene, and is associated with the predicted prognostic significance.

In the first step of the analysis, VOGs were identified from the microarray data. The maximum expression levels of probesets in non-neoplastic cases were determined ($B_{max}$, FIG. 2A). Probesets were identified that had mean expression levels in tumor samples that were at least 2-fold higher than $B_{max}$ in at least 10% (7 cases) of the tumors. In addition, it was required that the mean of the expression levels in the over-expressed cases ($\mu_T$) was 4-fold higher the mean of the expression levels in the non-neoplastic cases ($\mu_B$). Probesets that satisfied these two criteria were selected as VOGs for further analysis. The VOG analysis identified 270 probesets representing about 220 genes. TOP2a and ERG are examples of genes that met the criteria of the VOG analysis (FIG. 2B). Gene expression levels ranged from those in non-neoplastic cases to levels that were many-fold higher, even for tumors having the same Gleason pattern.

Figure 3:
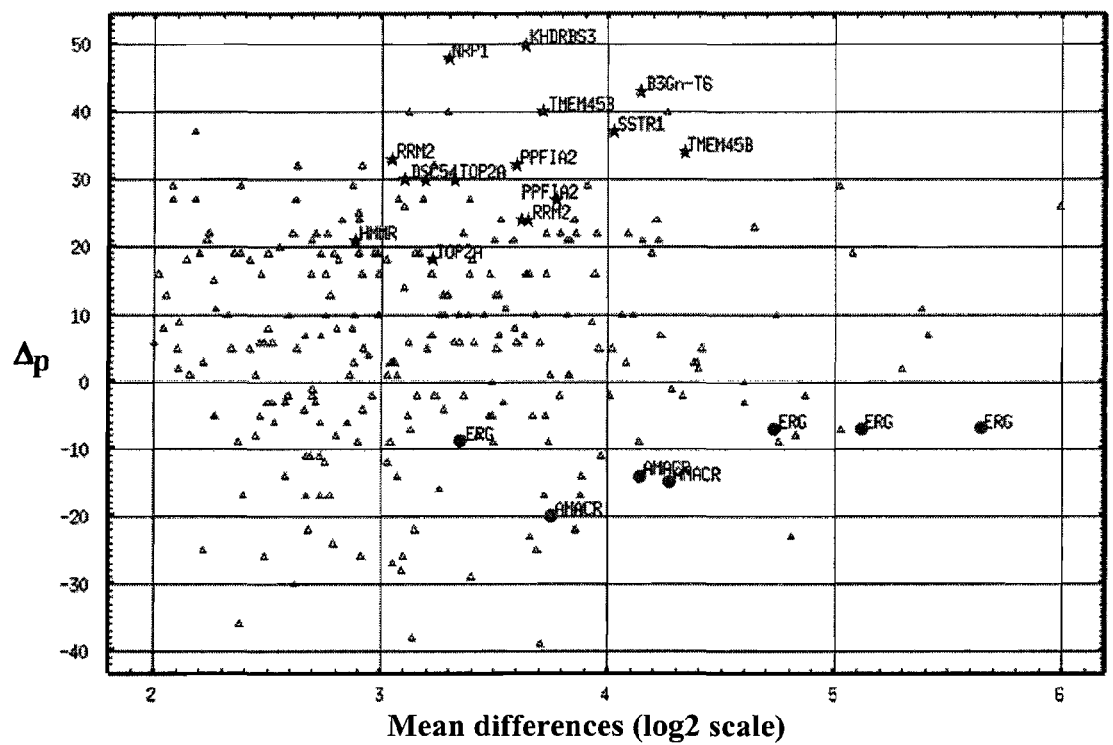
FIG. 3 is a graph plotting expression characteristics of probesets identified by VOG. The x-axis represents over-expression as defined in the VOG analysis, and the y-axis represents Δp. Stars indicate nucleic acids selected for validation. Dots indicate probesets for AMACR and ERG.

In the second step of the analysis, the percentage of aggressive ($P_{ag}$) and non-aggressive ($P_{nag}$) cases over-expressing each VOG was determined Aggressive tumors were represented by Gleason patterns 4 and 5 cases, and non-aggressive tumors were represented by Gleason pattern 3 cases. To identify probesets that are over-expressed in higher percentages of aggressive tumors and are therefore likely to have prognostic value, VOGs were ranked by $\Delta p$, where $\Delta p = P_{ag} - P_{nag}$. Mean differences in expression were plotted against $\Delta p$ for probesets selected by VOG (FIG. 3). The $\Delta p$ values varied widely among the over-expressed probesets, from negative −39 to positive +50. ERG and AMACR were observed to have negative $\Delta p$ values.

In the third step of the analysis, the size of the dataset was reduced by grouping probesets that had a similar pattern of expression across the 101 cases analyzed as described in Example 1. A Pearson's correlation was calculated for each probeset against all other probesets, and probesets that had a correlation coefficient greater than 0.5 were grouped into separate clusters.

The gene expression data were also analyzed using the p-value and fold change (pFC) approach, and results of this analysis were compared to results of the VOG analysis. Two sets of analyses were performed using fold change and p-values generated using dChip software. Probesets were selected that were detected as present in at least 40% of tumor cases, and that were over-expressed by at least 2.5-fold in tumor cases compared to non-neoplastic cases, with a p-value less than 0.0005. This comparison identified 248 probesets with a $90^{th}$ percentile false discovery rate (FDR) of 0%. Probesets were also selected that were detected as present in at least 40% of aggressive tumor cases (Gleason pattern 4 and 5) and that were over-expressed at least 2-fold in aggressive tumor cases compared to non-aggressive (Gleason pattern 3) tumor cases, with a p-value<0.0005. This comparison identified 122 probesets, with a $90^{th}$ percentile FDR of 1.6%.

Figure 4:
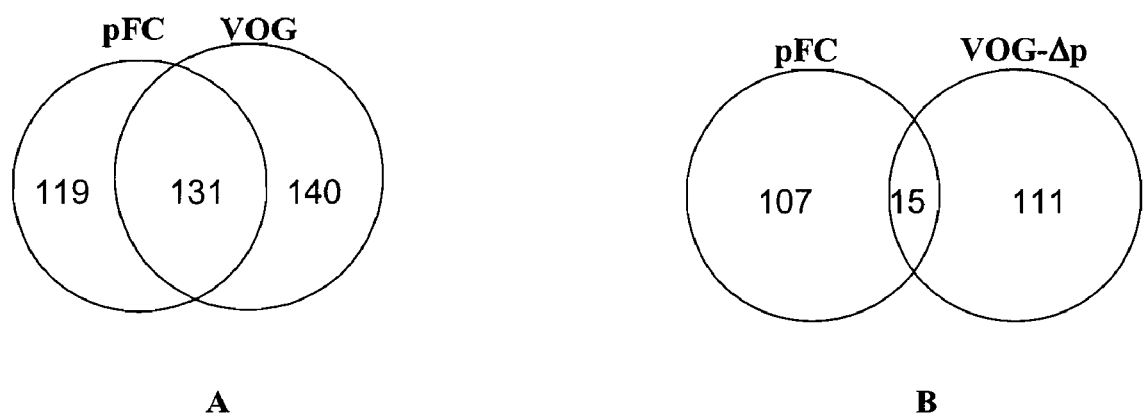
FIG. 4 contains two Venn diagrams depicting the overlap of nucleic acids selected using VOG approach or the pFC approach as being over-expressed in prostate cancer (FIG. 4A) or markers of prostate cancer aggressiveness (FIG. 4B).

To determine the overlap between the VOG approach and analysis by the pFC method, results were compared at two stages in the biomarker discovery process. First, the ability of VOG and pFC to identify over-expressed genes in tumor cells (step 1) was examined Analysis of the same expression data by both methods, comparing non-neoplastic tissues to all tumor tissue samples, identified similar numbers of candidates (FIG. 4a). The pFC method identified 250 over-expressed probe sets, and VOG identified 271 over-expressed probe sets. One hundred and thirty-one probe sets were identified by both methods (FIG. 4a). The second test was designed to determine how the methods compared in identifying markers of aggressiveness (FIG. 4b). The pFC method was used to compare non-aggressive (GP3) and aggressive (GP4 and GP5) tumors. This was analogous to the combined VOG-$\Delta p$. The pFC method identified 122 candidate probe sets, while VOG-$\Delta p$ identified 126. Overlap was limited to only about 15 probesets from either method. These results indicate that there is a relatively small overlap between the two selected lists of genes that may have prognostic value. It is likely that candidate genes identified by the VOG-$\Delta p$ approach would not have been selected by the more standard pFC method.

Figure 5:
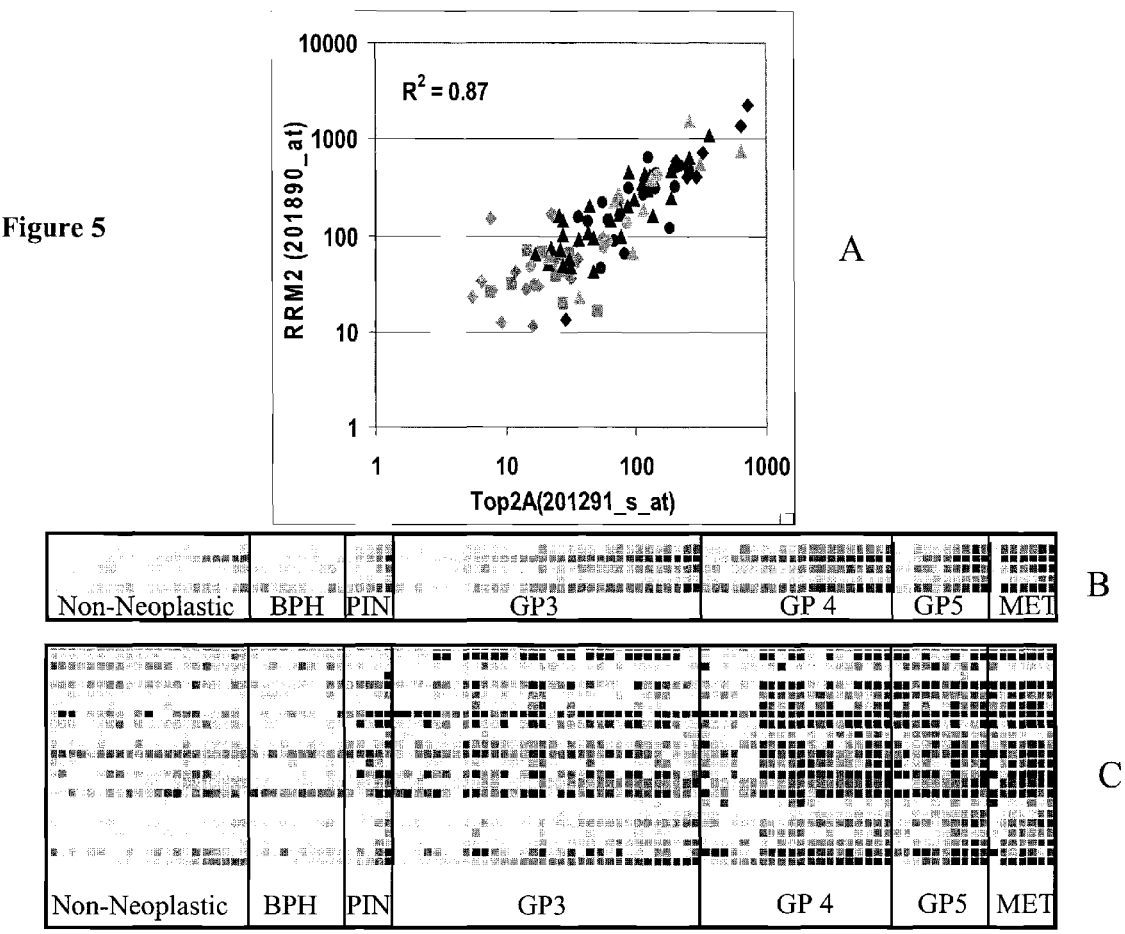
FIG. 5A is a graph plotting expression values of TOP2a against expression values of RRM2 in cancerous and non-cancerous prostate epithelial cells. The samples represent benign, PIN GP3, GP4, GP5, and metastasis samples.
FIG. 5B is a heat map depicting similar patterns of expression of different nucleic acids (intra-cluster probesets) across cancerous and non-cancerous prostate epithelial cells.
FIG. 5C is a heat map depicting different patterns of expression of different nucleic acids (inter-cluster probesets) across cancerous and non-cancerous prostate epithelial cells.

The VOG-$\Delta p$ list of candidates included probesets representing the same gene as well as probe sets representing different genes with similar expression patterns in the tissues studied. Grouping probesets based on a Pearson correlation of 0.7 for the expression patterns (FIG. 5) reduced the number of candidates to about 20 genes without loss of prognostic power. One cluster included Top2a and 59 probesets with similar expression patterns (Table 2). Most of the genes in this cluster encode proteins with a role in proliferation. FIG. 5a illustrates the correlation between two of these probesets, representing Top2a and RRM2. Many clusters were identified, each containing between about 2 to 50 different genes.

Example 3

Biomarker Validation

Genes that had high $\Delta p$ values or high expression levels in aggressive tumors were selected for validation. Gene expression was analyzed in formalin-fixed, paraffin-embedded (FFPE) tissues that were independent from the tissue samples used in nucleic acid expression profiling described above. The tissues were obtained from men who had a prostatectomy and at least five years of follow up information. Cases were defined as high-grade (Gleason score of 7 or higher) prostate cancer tissues from men who failed systemically within five years of prostatectomy. Controls were defined as high-grade prostate cancer tissues from men who did not have systemic progression seven years after their surgery. The case and control tissues were matched with respect to Gleason score, pre-operative PSA level, age, year of surgery, and margin, seminal vesicle and/or nodal invasion. One hundred pairs were randomly selected for validation experiments, and all samples for which tissue was available were used in the analysis (sixty-seven pairs). The laboratory personnel were blinded to case-control status, and processing of the samples was randomized to prevent experimental bias. With the exception of one sample, all of the remaining controls were free of systemic progression for at least eight years after surgery.

A section of each FFPE tissue was placed on a slide and stained with H&E. A pathologist circled the slide around the areas of the tumor tissue that had an aggressive phenotype. Subsequent sections (10 mm) of each tissue were prepared under RNase free conditions and deparaffinized with xylene. The identified tumor areas were scraped into 1.5 mL tubes containing digestion buffer from the RecoverAll kit (Ambion, Austin, Tex.). Total RNA was isolated according to the manufacturer's protocol. The isolated RNA was treated with DNase using the Turbo DNA free kit (Ambion)) according to the manufacturer's instructions. The amount of nucleic acid in each sample was measured using the Quant-iT™ RiboGreen kit (Invitrogen Carlsbad, Calif.). Reverse transcription was performed using Superscript III First Strand Synthesis system (Invitrogen) and 500 ng of RNA from each sample in 40 µL reaction volumes.

Quantitative PCR was performed using 12.5 ng of cDNA (RNA equivalents) per reaction in a 20 µL reaction volume with SYBR green PCR Master Mix (Applied Biosystems, Foster City, Calif.). An ABI 7900HT instrument was used with the manufacturer's default cycling conditions. The concentration of each primer was 0.15 or 0.2 nM. The primers were designed to amplify a 70-85 base pair fragment corresponding to the Affymetrix target sequence for the nucleic acid of interest. Primer Express software (ABI) was used in the primer design. The primer pairs were validated by generating standard curves using dilutions of pooled prostate cDNA from frozen cancerous and non-cancerous tissues and analysis of endpoint dissociation curves. GAPDH was amplified in each sample to verify that an adequate amount of amplifiable cDNA was present as a test for RNA quality. To check for genomic DNA contamination, RNA samples lacking reverse transcriptase were tested in a quantitative PCR reaction. Samples with a cycle threshold (Ct) less than 35 per 12.5 ng RNA were considered contaminated with DNA and were re-processed. Ct values above 35 were called "undetermined" and were manually set to 40 cycles for data analysis. For each sample, the average cycle number was used in data analysis.

Figure 6:
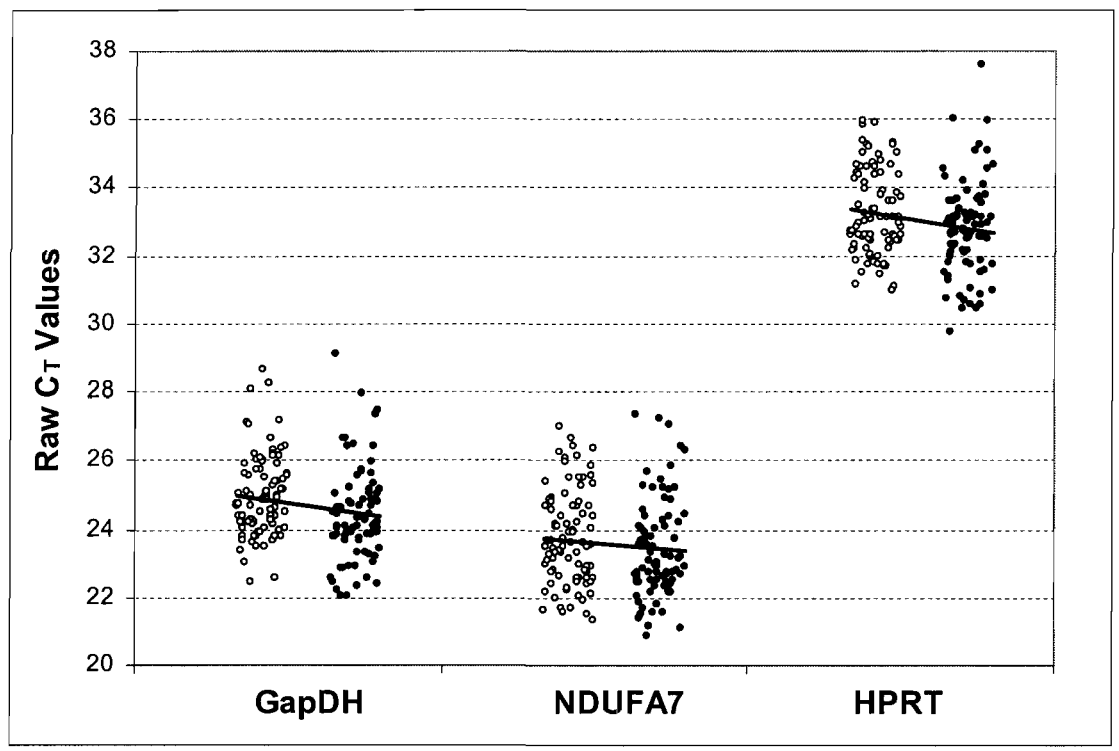
FIG. 6 is a graph plotting threshold cycles measured in the controls (open circles on the left) and the cases (closed circles on the right) by quantitative PCR using primers specific for GAPDH, HPRT, and NDUFA7. The solid line illustrates the linear regression between the two groups.

Suitable genes for normalization of quantitative PCR data were identified. The microarray data were searched for genes with minimum variation in expression across the 101 samples of cancerous and non-cancerous prostate epithelial cells analyzed as described in Example 1. The suitability of candidate genes was further assessed by analyzing the genes for minimum variation in expression across bulk kidney tissue samples. This was important because although candidate prostate cancer biomarkers were discovered using laser capture microdissected cells, further evaluation of the biomarkers was to be performed using bulk tissues. Candidate genes for normalization of quantitative PCR data were, therefore, analyzed for minimum variation in expression across various bulk kidney tissues that were profiled in another microarray study. This process identified NDUFA7 and RSP16 as the best genes for normalization. HPRT and GAPDH were also examined. These genes were ultimately assessed by quantitative RT-PCR of FFPE prostate samples in a case-control study. Among these genes, NDUFA7 produced the minimum variation across the cases and the controls (FIG. 6). More importantly, the average expression level for NDUFA7 had the smallest difference between the cases and the controls. NDUFA7 was, therefore, used as the normalizing gene in subsequent analyses.

Figure 7:
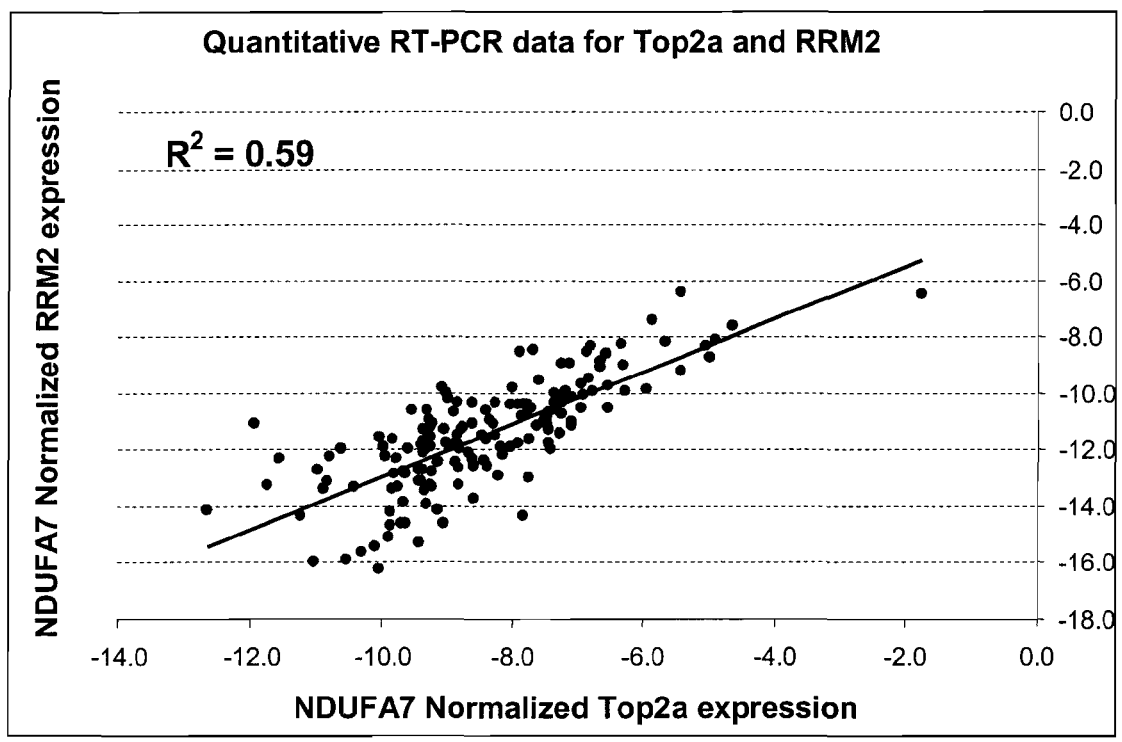
FIG. 7 is a graph plotting expression levels of RRM2 and Top2a normalized to expression of NDUFA7 ($\Delta C_{T\text{-}Normalized} = C_{T\text{-}NDUFA7} - C_{T\text{-}X}$, where X=RRM2 or Top2A. The data are from samples with low RNA degradation ($C_{T\text{-}NDUFA7} \leq 26$), which include over 90% of the case/control samples. $R^2=0.55$ when all samples are included.

The case-control tissue samples were analyzed for expression of genes with Δp values greater than 30 and genes with high Δp values and high expression levels in aggressive tumors. Four genes, RRM2, TOP2A, HSPC150, and CDC2, were identified as having Δp>30, and these genes were grouped in the same cluster (Table 2) by the data reduction step described in Example 2. RRM2 and Top2a were examined by quantitative PCR, and a significant correlation was observed between the expression levels of the two genes across the case-control samples ($R^2$=0.59, FIG. 7). This suggests that expression levels of these two genes, along with the other genes belonging to the same cluster, provide significantly overlapping information for prostate cancer outcome prediction.

Figure 8A:
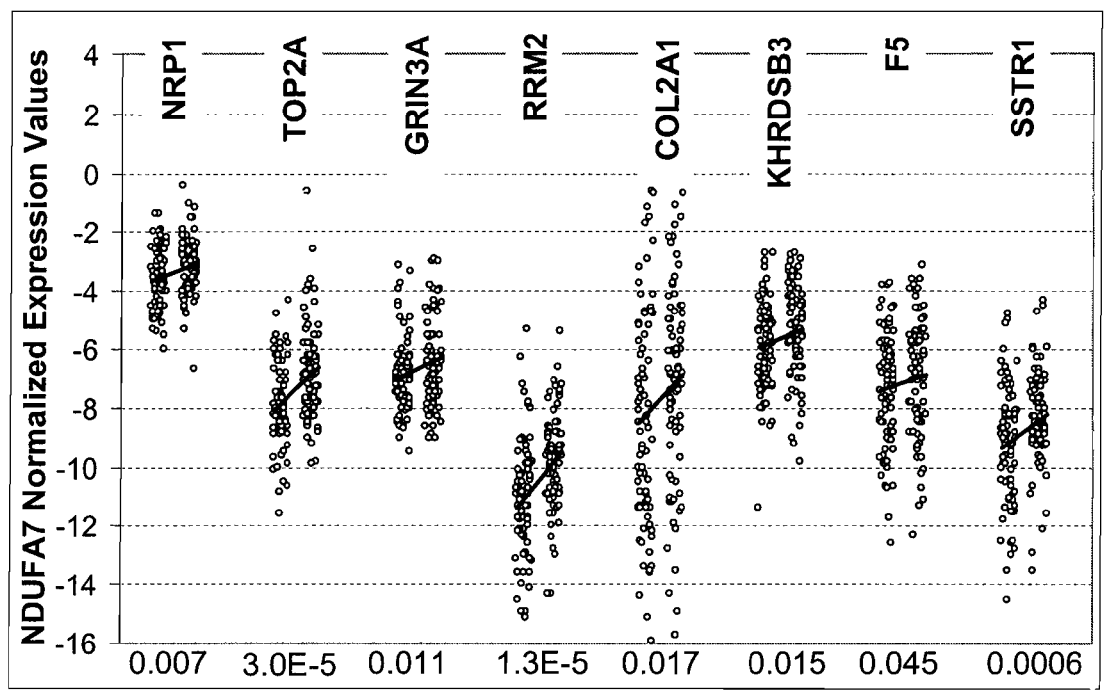
FIGS. 8A and 8B contain graphs plotting expression values of the indicated nucleic acids in cases (data points on the right) and controls (data points on the left) measured using quantitative PCR and normalized to NDUFA7 expression. Solid lines illustrate linear regression between cases and controls. The numbers along the bottom of the graph in FIG. 8A are p-values associated with a group t-test between cases and controls.

About 40% of the genes selected for quantitative RT-PCR validation had significantly higher expression levels in cases than controls (p<0.05; FIG. 8a and Table 1). Genes in the lower part of the table were not associated with systemic progression in this case control study.

It was determined whether the pFC method would have identified genes showing association with outcome in the case-control analysis. The 122 probesets identified by pFC comparison of non-aggressive versus aggressive tumors (FIG. 4b) were ranked by fold change (Table 1; rank 1 corresponds to highest fold change). Six of the eight genes listed in Table 1 as having significant association with outcome were not on the list generated by pFC (Table 1). These results indicate that VOG-Δp identified a set of candidates that was not likely to be identified by other means. More important, the VOG-Δp list includes candidates providing apparent prognostic information.

TABLE 1

Performance characteristics of selected genes

| Gene Name | Affy Probeset | Δp | pFC-rank | p-value (RT-PCR) |
|---|---|---|---|---|
| NRP1 | 210510_s_at | 48 | 15 | 0.007 |
| TOP2A | 201291_s_at | 30 | — | 2.9E−06 |
| GRIN3A | 233220_at | 21 | — | 0.011 |
| RRM2 | 209773_s_at | 33 | — | 1.3E−05 |
| COL2A1 | 213492_at | −2 | — | 0.017 |
| KHRDSB3 | 209781_s_at | 50 | — | 0.015 |
| F5 | 204714_s_at | 32 | — | 0.045 |
| SSTR1 | 235591_at | 37 | 7 | 0.0006 |
| PHCA | 222689_at | 37 | — | |
| B3GnT6 | 1552834_at | 43 | 63 | |
| DSC54 | 220014_at | 30 | — | |
| PPFIA2 | 206973_at | 32 | 1 | |
| HOXC6 | 206858_s_at | 40 | 84 | |
| Col10A1 | 217428_s_at | 40 | 23 | |
| C20orf102 | 226973_at | 40 | — | |
| TDO2 | 201291_s_at | 30 | — | |
| TMEM45 | 230323_s_at | 34 | — | |
| PTPRT | 205948_at | 19 | — | |
| CDH10 | 220115_s_at | 22 | — | |
| CDH7 | 220679_s_at | 22 | — | |
| AMACR | 209426_s_at | −14 | — | |
| ERG | 213541_s_at | −7 | — | |

Figure 8B:
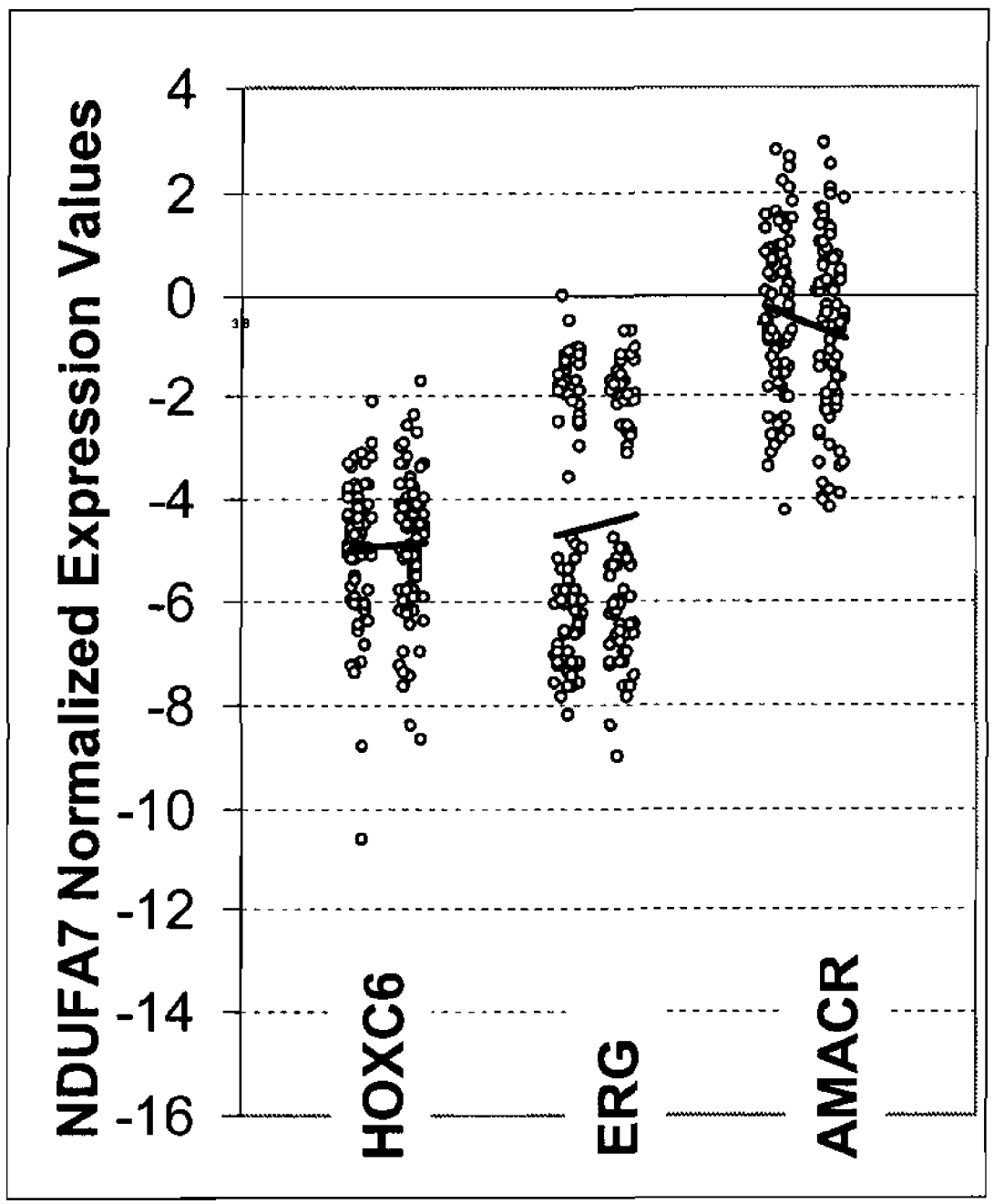

FIG. 8B is a plot of expression values of three genes that were not significantly associated with prostate cancer outcome. HOXC6 had a Δp value of 40 based on the microarray data. This gene was not validated in this case/control study. ERG and AMACR had Δp values of −14 and −7, respectively. The difference in ERG expression between cases and controls was not significant. A small decrease was observed in AMACR expression in cases with respect to controls (p<0.075). The quantitative RT-PCR data for ERG and AMACR were in agreement with the analysis based on Δp values.

TABLE 2

Genes correlated in expression with an RRM2 probe or a TOP2A probe

| GENE SYMBOL | AFFY PROBE | Correlation with RRM2 or TOP2A | GENBANK NAME | Chromosomal location | GENE NAME | Protein ID |
|---|---|---|---|---|---|---|
| NUSAP1 | 218039_at | 0.905196 | NM_016359 | chr15: 39412379-39460535 (+) // 97.13 // q15.1 | nucleolar and spindle associated protein 1 | NP_057443.1 /// NP_060924.4 |
| TOP2A | 201292_at | 0.8975574 | AL561834 | chr17: 35660692-35827676 (−) // 97.5 // q21.2 | topoisomerase (DNA) II alpha 170 kDa | NP_001058.2 |
| STK6 | 208079_s_at | 0.8775077 | NM_003158 | chr10: 115995747-115997400 (+) // 36.89 // q25.3 | serine/threonine kinase 6 | NP_003591.2 /// NP_940835.1 /// NP_940836.1 /// |

TABLE 2-continued

Genes correlated in expression with an RRM2 probe or a TOP2A probe

| GENE SYMBOL | AFFY PROBE | Correlation with RRM2 or TOP2A | GENBANK NAME | Chromosomal location | GENE NAME | Protein ID |
|---|---|---|---|---|---|---|
| KIF20A | 218755_at | 0.8732426 | NM_005733 | chr5: 137543246-137551259 (+) // 99.29 // q31.2 | kinesin family member 20A | NP_005724.1 |
| ASPM | 219918_s_at | 0.8712739 | NM_018123 | chr1: 193785048-193803423 (−) // 99.72 // q31.3 | asp (abnormal spindle)-like, microcephaly associated (*Drosophila*) | NP_060606.2 |
| MGC57827 | 225834_at | 0.8696505 | AL135396 | chr1: 120551068-120567723 (+) // 93.81 // p11.2 | Similar to RIKEN cDNA 2700049P18 gene | NP_997301.2 |
| RRM2 | 201890_at | 0.8686334 | BE966236 | chr2: 10213108-10222138 (+) // 88.99 // p25.1 | ribonucleotide reductase M2 polypeptide | NP_001025.1 |
| CDC2 | 203213_at | 0.864959 | AL524035 | chr10: 62208241-62224668 (+) // 95.12 // q21.2 | cell division cycle 2, G1 to S and G2 to M | NP_001777.1 /// NP_203698.1 |
| TOP2A | 201291_s_at | 0.8636451 | AU159942 | chr17: 35660692-35827676 (−) // 97.5 // q21.2 | topoisomerase (DNA) II alpha 170 kDa | NP_001058.2 |
| RRM2 | 209773_s_at | 0.8636451 | BC001886 | chr2: 10213479-10220523 (+) // 98.54 // p25.1 | ribonucleotide reductase M2 polypeptide | NP_001025.1 |
| CENPF | 207828_s_at | 0.8618696 | NM_005196 | chr1: 211164932-211225825 (+) // 97.04 // q41 | centromere protein F, 350/400ka (mitosin) | NP_057427.3 |
| PTTG1 | 203554_x_at | 0.8591274 | NM_004219 | chr5: 159781442-159788323 (+) // 97.53 // q33.3 | pituitary tumor-transforming 1 | NP_004210.1 |
| CCNB1 | 214710_s_at | 0.8549995 | BE407516 | chr5: 68498643-68509323 (+) // 93.33 // q13.2 | cyclin B1 | NP_114172.1 |
| CCNE2 | 205034_at | 0.8517452 | NM_004702 | chr8: 95961644-95975652 (−) // 98.41 // q22.1 | cyclin E2 | NP_004693.2 /// NP_477083.1 /// NP_477097.1 |
| CENPA | 204962_s_at | 0.8508387 | NM_001809 | chr2: 26920571-26929105 (+) // 99.93 // p23.3 | centromere protein A, 17 kDa | NP_001800.1 |
| MELK | 204825_at | 0.8451506 | NM_014791 | chr9: 36562872-36667678 (+) // 99.96 // p13.2 | maternal embryonic leucine zipper kinase | NP_055606.1 |
| — | 229490_s_at | 0.8443528 | AW271106 | chr1: 153308297-153308619 (+) // 79.41 // q22 | — | — |
| KIF4A | 218355_at | 0.8436775 | NM_012310 | chr5: 154373566-154377875 (+) // 93.49 // q33.2 | kinesin family member 4A | NP_036442.2 |
| BIRC5 | 202095_s_at | 0.8434663 | NM_001168 | chr17: 73721943-73732372 (+) // 97.65 // q25.3 | baculoviral IAP repeat-containing 5 (survivin) | NP_001159.1 |
| CCNB2 | 202705_at | 0.8426857 | NM_004701 | chr15: 57184611-57204535 (+) // 98.76 // q22.2 | cyclin B2 | NP_004692.1 |
| ZWINT | 204026_s_at | 0.8402275 | NM_007057 | chr10: 57787212-57791019 (−) // 98.25 // q21.1 | ZW10 interactor | NP_001005413.1 /// NP_001005414.1 /// |
| NUSAP1 | 219978_s_at | 0.8399199 | NM_018454 | chr15: 39412369-39437700 (+) // 98.15 // q15.1 | nucleolar and spindle associated protein 1 | NP_057443.1 /// NP_060924.4 |
| UHRF1 | 225655_at | 0.838659 | AK025578 | chr12: 20595770-20598590 (+) // 69.8 // p12.2 | ubiquitin-like, containing PHD and RING finger domains, 1 | NP_037414.2 |
| HSPC150 | 223229_at | 0.8381478 | AB032931 | chr1: 199032607-199036581 (−) // 99.85 // q32.1 | HSPC150 protein similar to ubiquitin-conjugating enzyme | NP_054895.1 |
| ZNF367 | 229551_x_at | 0.8379291 | N62196 | chr9: 96227777-96228204 (−) // 90.54 // q22.32 | zinc finger protein 367 | NP_710162.1 |
| HCAP-G | 218663_at | 0.8372119 | NM_022346 | chr4: 17488873-17521400 (+) // 99.75 // p15.32 | chromosome condensation protein G | NP_071741.2 |
| FLJ23311 | 219990_at | 0.8361087 | NM_024680 | chr11: 19202189-19210494 (−) // 94.6 // p15.1 | FLJ23311 protein | NP_078956.2 |
| CDC2 | 210559_s_at | 0.8359027 | D88357 | chr10: 62209903-62223768 (+) // 99.62 // q21.2 | cell division cycle 2, G1 to S and G2 to M | NP_001777.1 /// NP_203698.1 |
| PRC1 | 218009_s_at | 0.832837 | NM_003981 | chr15: 89310278-89338729 (−) // 97.96 // q26.1 | protein regulator of cytokinesis 1 | NP_003972.1 /// NP_955445.1 /// NP_955446.1 |
| STK6 | 204092_s_at | 0.8278999 | NM_003600 | chr20: 54377851-54400656 (−) // 99.2 // q13.31 | serine/threonine kinase 6 | NP_003591.2 /// NP_940835.1 /// NP_940836.1 |
| CDC20 | 202870_s_at | 0.825828 | NM_001255 | chr1: 43493720-43497964 (+) // 96.44 // p34.2 | CDC20 cell division cycle 20 homolog (*S. cerevisiae*) | NP_001246.1 |
| KIF2C | 209408_at | 0.8245021 | U63743 | chr1: 44874643-44902453 (+) // 99.85 // p34.1 | kinesin family member 2C | NP_006836.1 |
| UBE2C | 202954_at | 0.8228344 | NM_007019 | chr20: 43874709-43878997 (+) // 96.55 // q13.12 | ubiquitin-conjugating enzyme E2C | NP_008950.1 /// NP_861515.1 /// NP_861516.1 /// |

TABLE 2-continued

Genes correlated in expression with an RRM2 probe or a TOP2A probe

| GENE SYMBOL | AFFY PROBE | Correlation with RRM2 or TOP2A | GENBANK NAME | Chromosomal location | GENE NAME | Protein ID |
|---|---|---|---|---|---|---|
| BUB1B | 203755_at | 0.8218721 | NM_001211 | chr15: 38240671-38300613 (+) // 99.19 // q15.1 | BUB1 budding uninhibited by benzimidazoles 1 homolog beta (yeast) | NP_001202.4 |
| DLG7 | 203764_at | 0.8189188 | NM_014750 | chr14: 54684600-54725528 (−) // 99.89 // q22.3 | discs, large homolog 7 (*Drosophila*) | NP_055565.2 |
| KIAA0101 | 202503_s_at | 0.8183023 | NM_014736 | chr15: 62444842-62460684 (−) // 100.0 // q22.31 | KIAA0101 | NP_055551.1 |
| LMNB1 | 203276_at | 0.8180022 | NM_005573 | chr5: 126141099-126200603 (+) // 98.88 // q23.2 | lamin B1 | NP_005564.1 |
| KPNA2 | 211762_s_at | 0.8169924 | BC005978 | chr17: 63462312-63473205 (+) // 98.04 // q24.2 | karyopherin alpha 2 (RAG cohort 1, importin alpha 1) | NP_002257.1 |
| TPX2 | 210052_s_at | 0.8166038 | AF098158 | chr20: 29790791-29852956 (+) // 98.58 // q11.21 | TPX2, microtubule-associated protein homolog (*Xenopus laevis*) | NP_036244.2 |
| KIF23 | 204709_s_at | 0.8125979 | NM_004856 | chr15: 67493741-67527817 (+) // 98.34 // q23 | kinesin family member 23 | NP_004847.2 /// NP_612565.1 |
| DKFZp762E1312 | 218726_at | 0.8122278 | NM_018410 | chr2: 234528028-234532668 (−) // 98.77 // q37.1 | hypothetical protein DKFZp762E1312 | NP_060880.2 |
| C10orf3 | 218542_at | 0.8086163 | NM_018131 | chr10: 95249894-95278837 (+) // 99.78 // q23.33 | chromosome 10 open reading frame 3 | NP_060601.2 |
| CDC2 | 203214_x_at | 0.8053681 | NM_001786 | chr10: 62208241-62223768 (+) // 98.76 // q21.2 | cell division cycle 2, G1 to S and G2 to M | NP_001777.1 /// NP_203698.1 |
| RACGAP1 | 222077_s_at | 0.8033648 | AU153848 | chr12: 48669213-48669853 (−) // 94.13 // q13.12 | Rac GTPase activating protein 1 | NP_037409.2 |
| CDCA3 | 223307_at | 0.802792 | BC002551 | chr12: 6828253-6830687 (−) // 97.47 // p13.31 | cell division cycle associated 3 | NP_112589.1 |
| CDKN3 | 1555758_a_at | 0.8013917 | AF213040 | chr14: 53936360-53948102 (+) // 96.81 // q22.2 | cyclin-dependent kinase inhibitor 3 (CDK2-associated dual specificity phosphatase) | NP_005183.2 |
| HMMR | 207165_at | 0.801 | NM_012485 | chr5: 162820240-162851523 (+) // 95.27 // q34 | hyaluronan-mediated motility receptor (RHAMM) | NP_036616.1 /// NP_036617.1 |
| TYMS | 202589_at | 0.7881706 | NM_001071 | chr18: 647650-663492 (+) // 96.88 // p11.32 | thymidylate synthetase | NP_001062.1 |
| STMN1 | 200783_s_at | 0.7541283 | NM_005563 | chr1: 25910753-25917050 (−) // 99.93 // p36.11 | stathmin 1/oncoprotein 18 | NP_005554.1 /// NP_981944.1 /// NP_981946.1 |
| CDKN3 | 209714_s_at | 0.749007 | AF213033 | chr14: 53936360-53956576 (+) // 98.51 // q22.2 | cyclin-dependent kinase inhibitor 3 | NP_005183.2 |
| HMMR | 209709_s_at | 0.7424729 | U29343 | chr5: 162820238-162851265 (+) // 98.88 // q34 | hyaluronan-mediated motility receptor (RHAMM) | NP_036616.1 /// NP_036617.1 |
| ANLN | 222608_s_at | 0.736583 | AK023208 | chr7: 36202720-36266640 (+) // 96.26 // p14.2 | anillin, actin binding protein (scraps homolog, *Drosophila*) | NP_061155.2 |
| MLF1IP | 218883_s_at | 0.7343241 | NM_024629 | chr4: 185991306-186025313 (−) // 95.75 // q35.1 | MLF1 interacting protein | NP_078905.2 |
| TK1 | 202338_at | 0.7281973 | NM_003258 | chr17: 73681775-73694726 (−) // 99.65 // q25.3 | thymidine kinase 1, soluble | NP_003249.1 |
| HCAP-G | 218662_s_at | 0.7228633 | NM_022346 | chr4: 17488873-17521400 (+) // 99.75 // p15.32 | chromosome condensation protein G | NP_071741.2 |
| MKI67 | 212022_s_at | 0.713936 | BF001806 | chr10: 129784916-129814639 (−) // 97.55 // q26.2 | antigen identified by monoclonal antibody Ki-67 | NP_002408.2 |
| C13orf3 | 227165_at | 0.7103539 | AI829603 | chr13: 20625734-20648824 (−) // 90.4 // q12.11 | chromosome 13 open reading frame 3 | NP_659498.2 |
| PBK | 219148_at | 0.706868 | NM_018492 | chr8: 27723331-27751219 (−) // 98.77 // p21.1 | PDZ binding kinase | NP_060962.2 |
| FLJ11029 | 228273_at | 0.7052626 | BG165011 | chr17: 54636997-54640015 (+) // 48.4 // q23.2 | Hypothetical protein FLJ11029 | NP_060774.1 |

Example 4

Biomarker Validation Using Only Non-Invasive Controls

The results described in Example 3 were obtained using case and control tissues that were matched with respect to clinical parameters, including margin, seminal vesicle and/or nodal invasion. When only non-invasive controls were included in the case/control study, additional genes with prognostic value were identified (Table 3). These genes can serve as prognostic biomarkers in biopsy tissues, where invasive status is not known.

TABLE 3

Comparison of the significance of differential expression between cases and controls that do or do not include tissues from invasive tumors

| Gene | T-TEST p-value cases vs. all controls | T-TEST p-value cases vs. non-invasive controls | Description | Representative Refseq | Alternate Gene Symbols | Protein |
|---|---|---|---|---|---|---|
| NRP1 | 0.006682 | 0.001525 | neuropilin 1 | NM_003873 | AB209641, AF016050, AF018956, BX510902, CR749333, NRP, VEGF165R, | O14786 NRP1_HUMAN |
| TOP2A | 0.000003 | 0.000030 | DNA topoisomerase II, alpha isozyme | NM_001067 | J04088, TOP2 | P11388 (aka TOP2A_HUMAN) |
| GRIN3A | 0.010939 | 0.023458 | glutamate receptor, ionotropic | NM_133445 | AB075853, AF416558, AJ416950, KIAA1973 | Q8TCU5 (aka NMD3A_HUMAN or NM3A_HUMAN) |
| RRM2 | 0.000013 | 0.000006 | ribonucleotide reductase M2 polypeptide | NM_001034 | BC001886, BC030154, CR590959, CR596700, CR602054, CR602150, CR603461, CR604378, CR608076, CR609838, CR614990, CR618451, CR621427, CR625489, RR2, S40301, X59618 | P31350 (aka RIR2_HUMAN) |
| COL2A1 | 0.016989 | 0.000803 | alpha 1 type II collagen isoform 1 | NM_001844 | SEDC | P02458 (aka CO2A1_HUMAN or CA12_HUMAN) |
| KHRDSB3 | 0.015472 | 0.008026 | KH domain containing, RNA binding, signal | NM_006558 | AF051321, AF069681, BC032606, BC068536, CR591014, Etle, etoile, SALP, SLM-2, SLM2, T-STAR, T-Star | O75525 |
| F5 | 0.044672 | 0.013952 | coagulation factor V precursor | NM_000130 | M14335, M16967 | P12259 (aka FA5_HUMAN) |
| SSTR1 | 0.000622 | 0.001906 | somatostatin receptor 1 | NM_001049 | BC035618 | P30872 (aka SSR1_HUMAN) |
| Col10A1 | 0.075196 | 0.085830 | collagen, type X, alpha 1 precursor | NM_000493 | | Q03692 (aka COAA1_HUMAN or CA1A_HUMAN) |
| C20orf102 | 0.185550 | 0.065311 | hypothetical protein LOC128434 | NM_080607 | AK056177, AL834410, BC033818, dJ1118M15.2 | Q96N03 (aka CT102_HUMAN or CTX2_HUMAN) |
| SERPINI1 | 0.126510 | 0.010822 | serine (or cysteine) proteinase inhibitor, clade | NM_005025 | BC018043, CR627434, neuroserpin, PI12, Z81326 | Q99574 (aka NEUS_HUMAN) |
| TDO2 | 0.139696 | 0.038706 | tryptophan 2,3-dioxygenase | NM_005651 | BC005355, TDO, U32989 | P48775 (aka T23O_HUMAN) |
| CDH10 | 0.001906 | 0.013692 | cadherin 10, type 2 preproprotein | NM_006727 | AB035303, AF039747 | Q9Y6N8 (aka CAD10_HUMAN or CADA_HUMAN) |
| HDAC9 | 0.178586 | 0.079474 | histone deacetylase 9 isoform 4 | NM_178423 | AJ459808, HDAC7, HDAC7B, KIAA0744 | Q9UKV0 (aka HDAC9_HUMAN or HDA9_HUMAN) |
| PCDHB10 | 0.062464 | 0.016364 | protocadherin beta 10 precursor | NM_018930 | AF152489, AF217748, AK056391, AY358720, BC031837 | Q9UN67 (aka PCDBA_HUMAN or CDBA_HUMAN) |

Example 5

A Gene Expression Profile Predictive of Outcome in Men at High-Risk of Systemic Progression and Death from Prostate Cancer Following Radical Retropubic Prostatectomy Cohort Study for Endorsing High-Risk Population Marker Development To confirm the need for novel biomarkers to predict outcome in high risk prostate cancer patients, an analysis of a cohort of prostate cancer patients was undertaken. This cohort analysis was performed independent of the case-control study used to evaluate the candidate biomarkers. This analysis, used the Mayo Radical Prostatectomy database cases from 1990-2004, where 441 systemic progressions were observed in 10,626 patients initially treated with RRP. From this data, a Cox proportional hazards model was computed using only existing clinical and pathologic parameters as predictors. Independent analyses were performed on the entire cohort and on the high risk subgroup (GS≧7).

Validation 1 Case-Control Design

The records of all men treated by RRP at the Mayo Clinic between 1990 and 1999, with archived paraffin-embedded material from the RRP specimen, were examined. Men with systemic progression within five years of RRP were identified, and matched with controls known to be free of systemic progression at seven years. Subjects were also matched on Gleason score, TNM stage, margin status, and preoperative serum PSA. Patients undergoing RRP at the Mayo Clinic were evaluated postoperatively at least quarterly for one year, semiannually for one year, and annually thereafter. Digital rectal examination and serum PSA were evaluated at each visit. If patients had an abnormal elevation in serum PSA postoperatively, a radioactive bone scan, plain radiograph in the presence of an abnormal bone scan, and/or computerized tomography were performed. Patients that did not return to the Mayo Clinic were mailed kits for blood submission and serum PSA testing, and additional medical information was obtained from the local physicians as needed (Blute et al., *J. Urol.*, 165(1):119-25 (2001)). Systemic progression was defined as the development of metastatic disease as determined by clinical, radiologic (bone or CT scan), or pathologic (biopsy) evaluation. PSA progression alone was not sufficient for declaration of a systemic progression. Based on this data, a set of 200 (initially) samples, comprising matched cases and controls, was defined. Tissues were acquired from the tissue bank and reviewed by two pathologists blinded to the case-control status. 76 cases and 81 controls passed the pathology review and had sufficient tissue sample available for experimental analysis. The clinical and pathologic features of the selected subjects were noted (Table 4). Due to the exclusion of several subjects following review by the pathologists, exact case-control matching was not preserved. However, the retained cases and controls remained balanced on age, preoperative serum PSA, TNM stage, Gleason score, margin status, and adjuvant (<90 days after surgery) therapy, and an unmatched analysis was used. Based on the final numbers, the study had about 80% power to detect (alpha=0.05, two-sided) a mean difference in gene expression between cases and controls equivalent to 0.45 standard deviations. For present/absent gene expression, a 22 percentage point difference (e.g., 40% vs. 62%) between cases and controls could be detected.

TABLE 4

The clinical and pathologic features of the patients in the case-control study.

| Feature | Case (N = 76) | Control (N = 81) | p value |
|---|---|---|---|
| Age at Surgery | | | 0.24 |
| Mean (SD) | 65.3 (6.8) | 64.0 (6.77) | |
| Median | 67 | 65 | |
| Range | (47.0-78.0) | (48.0-77.0) | |
| Preop PSA (ng/mL) | | | 0.97 |
| Median | 10.1 | 12 | |
| Q1, Q3 | 6.1, 23.1 | 6.9, 24.6 | |
| Range | (1.3-143.0) | (1.7-119.0) | |
| Gleason Score | | | 0.35 |
| 7 | 43 (56.6%) | 42 (51.9%) | |
| 8+ | 33 (43.4%) | 39 (48.1%) | |
| Pathologic Stage, 1997 TNM | | | 0.23 |
| T2aN0 | 8 (10.5%) | 9 (11.1%) | |
| T2bN0 | 11 (14.4%) | 18 (22.2%) | |
| T34N0 | 44 (57.9%) | 38 (46.9%) | |
| TxN+ | 13 (17.1%) | 16 (19.7%) | |
| Margin Positive | 51 (67.1%) | 50 (61.7%) | 0.27 |
| Ploidy | | | <0.001 |
| Diploid | 26 (34.2%) | 42 (51.9%) | |
| Tetraploid | 31 (40.8%) | 33 (40.7%) | |
| Aneuploid | 19 (25%) | 6 (7.4%) | |
| Adjuvant Hormonal Treatment | 27 (35.5%) | 27 (33.3%) | 0.77 |
| Adjuvant Radiation Treatment | 11 (14.5%) | 12 (14.8%) | 0.95 |

Validation 2 Case-Control Design

An independent nested-case control validation study was conducted using 21 systemic progression patients (cases) from the fresh frozen prostatectomy cohort from 2000-2005 inclusive. Controls were selected from those at risk at the time of the case's event and matched on Gleason score, pathologic stage, age, and year of surgery. The risk-set sampling design was preferred since the follow-up time was not sufficient to select 7-year systemic-progression-free matched controls. Four potential controls were identified with the first one or two that qualified selected for further experimental processing. The total number of controls with sufficient RNA was 36.

Processing of Formalin Fixed Paraffin Embedded (FFPE) Samples

In all experiments, the processing of samples was randomized to prevent processing biases. Each case was reviewed by a pathologist, and tumor was identified on H-E stained sections. Subsequent sections (10 µm) from each case were prepared under RNase free condition and de-paraffinized with Xylene. Identified tumor areas were scraped into 2 mL tubes containing digestion buffer (RecoverAll kit, Ambion, Austin, Tex.). Total RNA was isolated according to the RecoverAll RNA isolation procedure. The isolated RNA was treated with DNase using Ambion Turbo DNA free kit, according to the manufacturer's instructions (Ambion). The amount of RNA in each case was measured by the Quant-iT™ RiboGreen kit (Invitrogen Carlsbad, Calif.). Reverse transcription was performed using Superscript III First Strand Synthesis system (Invitrogen) and 500 ng of RNA from each case in a 40 µL reaction volume.

Processing of Frozen Samples for Validation

Tissue was cut by the tissue-processing core facility and not allowed to thaw. Sections were stored on slides at −80° C. for less than one week. Slides were placed directly from −80° C. to 75% ethanol (ETOH) for 30 seconds×2 to remove optimum cutting temperature (OCT) compound (Tissue-Tek), then placed in 95% ETOH for 30 seconds and 100% ETOH for 30 seconds and air dried. Tissue was scraped directly into lysis solution from the RNeasy mini or midi kit (Qiagen, Valencia, Calif.) and processed immediately according to manufacturer's instructions. Reverse transcription and qPCR were performed as described for FFPE tissue except 200 ng of RNA was used in the RT reaction and 1 µL cDNA was used in subsequent qPCR (5 ng RNA equivalent).

Quantitative PCR (qPCR) was performed on each sample by adding 12.5 ng total RNA equivalent of cDNA to a 20-µL reaction volume for each gene of interest using SYBR green PCR Master Mix (Applied Biosystems ABI, Foster City, Calif.) on the ABI 7900HT real time PCR machine using the manufacturer's default cycling conditions. Primers for qPCR were designed using Primer Express software (ABI) to amplify a 70-85 base pair fragment from the Affymetrix target sequence for the gene of interest. The primer pair concentrations (0.15 or 0.2 µM final) were optimized by generating standard curves using a pool of prostate cDNA from normal and tumor tissue. To check for genomic DNA, No-RT samples were run in a qPCR reaction and those with cycle threshold (Ct) less than 35 for GapDH were considered contaminated with DNA and were re-processed. In the analysis of data, "undetermined" values for Cts were replaced with a Ct of 40, which was the maximum cycle number in the qPCR experiments. All samples were analyzed in duplicate, and all studies were carried out under approved protocols. Primers used for the quantitative RT-PCR expression analysis of the genes in the final model are:

```
                               (SEQ ID NO: 1)
GAPDH Forward:    5'-CATGGCCTCCAAGGAGTAAGAC-3'

(SEQ ID NO: 2)
GAPDH Reverse:    5'-TCTCTTCCTCTTGTGCTCTTGCT-3'

(SEQ ID NO: 3)
RPS 28 Forward:   5'-GCTGCTCGCTGGGTCTTG-3'

(SEQ ID NO: 4)
RPS 28 Reverse:   5'-GGAGCAGATTGTGACAGACCATT-3'
```

-continued

| | | |
|---|---|---|
| ERG Forward: | 5'-GCTGCCACAATCAGAAATCA-3' | (SEQ ID NO: 5) |
| ERG Reverse: | 5'-TCGCGACTCAAAGGAAAACT-3' | (SEQ ID NO: 6) |
| TOP2A Forward: | 5'-TGGCTGCCTCTGAGTCTGAA-3' | (SEQ ID NO: 7) |
| TOP2A Reverse: | 5'-AGTCTTCTGCAATCCAGTCCTCTT-3' | (SEQ ID NO: 8) |
| CDH10 Forward: | 5'-GAACAGGATAGTTCTCCCTTAAGCA-3' | (SEQ ID NO: 9) |
| CDH10 Reverse: | 5'-CAAGGGCAGGACATGTACCTAAC-3' | (SEQ ID NO: 10) |
| ETV1 Forward: | 5'-TGTTTTTGCTTTGCATTTGG-3' | (SEQ ID NO: 11) |
| ETV1 Reverse: | 5'-TCCCCATTTACTCATGGTTTTT-3' | (SEQ ID NO: 12) |
| ETV4 Forward: | 5'-GCAGATCCCCACTGTCCTAC-3' | (SEQ ID NO: 13) |
| ETV4 Reverse: | 5'-CCACTTTTCCTTCCCAATGA-3' | (SEQ ID NO: 14) |

Data Analysis

All quantitative PCR measurements were normalized by subtracting the number of cycles measured for a candidate gene from the average number of cycles measured for GAPDH and RPS28 in the same tissue sample. This normalization method inverts the amplification values, such that higher values correspond to higher expression. The full set of un-normalized data was used to assess the variance of the assay using a Bland-Altman plot of the average of a pair of replicates versus their difference. Assay variability was close to constant for values below 33, from which point it increased linearly. The inverse of the estimated variance was used to create a weighted average for each replicate pair. In samples where one replicate measure returned no value, the other replicate value was used. In samples where both replicate measures returned no value, the measurement was treated as missing.

Fusion Status Analysis

The presence of TMPRSS2-ERG, TMPRSS2-ETV1, and TMPRSS2-ETV4 fusions was assigned based the expression values of ERG, ETV1, and ETV4 genes. The thresholds for status assignments were determined for each gene by analyzing the normalized CT expression values of these genes. Samples where the expression was greater than the upper threshold in any of the three genes (ERG>−4.8, ETV1>−5.5, ETV4>−6) were designated fusion positive. Samples where the expression was less than the lower threshold for all three genes (ERG<−5.4, ETV1<−6.8, ETV4<−5.9) were assigned fusion negative. All other samples were assigned an undetermined status. A discrete variable was then used to denote the predicted fusion status of the cases and controls by assigning a "1" to fusion+ samples, a "−1" to fusion− samples, and a "0" to the samples with undetermined status.

Ploidy Analysis

Flow cytometry was performed as described elsewhere (Zanetta et al., Am. J. Obstet. Gynecol., 175(5):1217-25 (1996)). The nuclear content of 10,000 nuclei was measured with a FACScan (Becton Dickinson, Sunnyvale, Calif.) flow cytometer. Cell cycle evaluation of the DNA histogram was performed with a Modfit 5.2 (Verity Software, Topsham, Me.) computerized software program. Tumors with only one identifiable gap0-gap1 peak were classified as DNA diploid (2n). Tumor samples that contained a significant increase in the 4n peak (more than 9% of nuclei) and an identifiable 8n population were categorized as DNA tetraploid. Tumor DNA content was classified as DNA aneuploid if a separate, identifiable gap0-gap1 peak was present. All DNA histograms were analyzed and classified without knowledge of the clinicopathologic features or patient outcome. The ploidy status parameter was defined as 0 for diploid tumors, 1 for tetraploid tumors, and 2 for anauploid.

Statistical Methods

In the cohort study, the Cox proportional hazards model was used to evaluate predictors of time to systemic progression. The concordance statistic (C), which has an interpretation similar to ROC curve area, was used to compare models. In the case-control study, the association of gene expression with systemic progression was assessed using univariate and multivariate logistic regression with the dependent variable (0=control, 1=case) and the normalized genes as the independent predictors. Computations were done using the S-Plus statistical package (Insightful Corp, Seattle Wash.) and the open-source R statistical package. The clustering analysis was performed using clustering methods in R.

Results

Cohort Study for Current High-Risk Prostate Cancer Marker Status

The study objective was to generate a multivariate molecular model that would add value to contemporary prognostic factors in predicting adverse outcomes. Using patients treated from 1990-2004 in the Mayo Radical Prostatectomy database, the Cox proportional hazards model was used to identify significant clinical predictors of time to systemic progression. The strongest predictors were RRP Gleason score, pathologic stage components (extra-capsular cancer, seminal vesicle involvement, lymph node metastases), and the use of adjuvant (within 90 days after RRP) hormonal therapy (Table 5). The model had a ROC area under the curve (as measured by the concordance statistic) of 0.82. Gleason score was the strongest predictor with ten year rates of systemic progression for GS 2-6, 7, and 8-10 of 1.9%, 10.6% and 23.6%, respectively. When the patient cohort was restricted to GS 7-10, the strongest significant clinical predictors of time to systemic progression were RRP Gleason score, seminal vesicle involvement, and lymph node involvement (Table 5), and the concordance statistic dropped to 0.69. Guided by these results, it was concluded that a high-risk prostate cancer RRP population, with GS≧7, would strongly benefit from molecular marker panels to improve prognostic predictions. To address this need, a case-control study was designed to identify molecular markers using GS≧7 patients with and without systemic progression. Cases were defined as men that developed systemic progression or died of prostate cancer within five years of RRP matched for Gleason score, TNM stage, margin status and preoperative serum PSA with controls that did not develop systemic progression or die of prostate cancer.

TABLE 5

Multivariate (Cox model) analysis of clinical and pathologic predictors of systemic progression after RRP from the Mayo Clinic RRP database of 10,626 men.

| | All Gleason Scores | | Gleason Score 7-10 | |
|---|---|---|---|---|
| Variable | Hazard Ratio | P-value | Hazard Ratio | P-value |
| Gleason 7 | 4.0 (vs. 2-6) | <0.0001 | NA | — |
| Gleason 8-10 | 8.5 (vs. 2-6) | <0.0001 | 2.2 (vs. 7) | <.0001 |
| Extra-capsular extension | 1.7 | <0.0001 | 1.2 | 0.26 |

TABLE 5-continued

Multivariate (Cox model) analysis of clinical and pathologic predictors of systemic progression after RRP from the Mayo Clinic RRP database of 10,626 men.

| Variable | All Gleason Scores | | Gleason Score 7-10 | |
|---|---|---|---|---|
| | Hazard Ratio | P-value | Hazard Ratio | P-value |
| Seminal vesicle involvement | 2.9 | <0.0001 | 2.6 | <0.0001 |
| Nodal involvement | 1.6 | 0.002 | 1.5 | .030 |
| Adjuvant hormonal therapy | 0.7 | 0.005 | 0.8 | 0.076 |
| N (events) | 10626 (441) | | 3636 (335) | |
| Concordance statistic | 0.82 | | 0.69 | |

Case-Control Study

Figure 9:
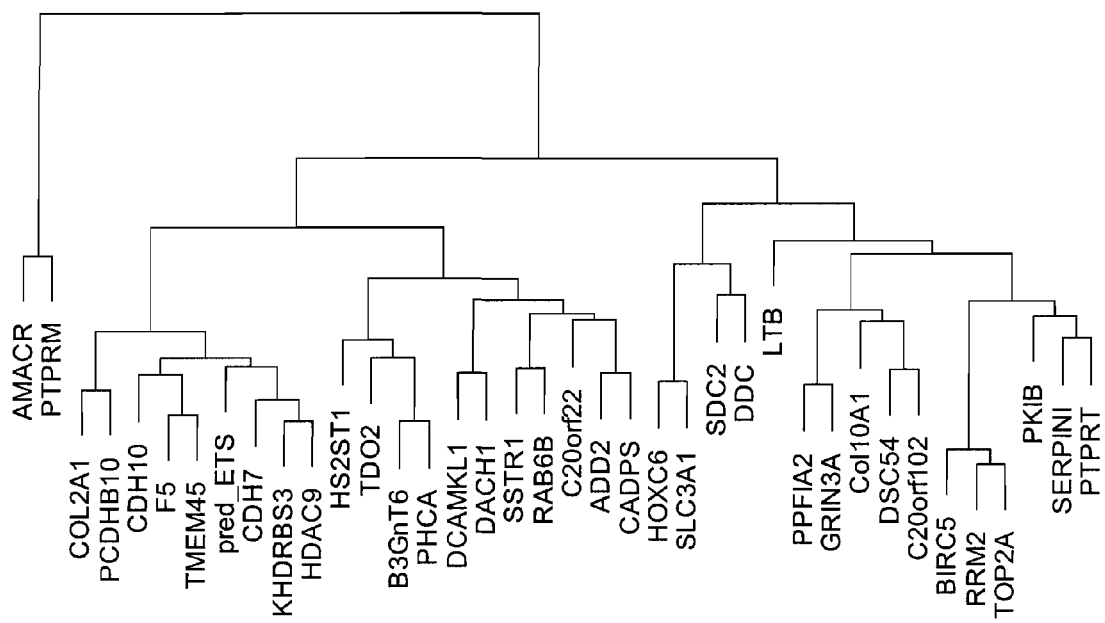
FIG. 9 is a gene cluster diagram of nucleic acids clustered using functions from the R package according to their expression profiles in all samples. Expression vectors were first centered according to the mean expression for each nucleic acid. Then, the distance matrix was computed using Pearson correlation as the distance measure. The clustering was performed using "hclust" with default parameters. Most of the nucleic acids clustered into two major clades. The three proliferation related nucleic acids, BIRC5, TOP2A, and RRM2, are the closest subcluster.

The cases and controls were very similar in their clinical and pathologic features with the exception of DNA ploidy. The gene expression pattern between the two groups was evaluated using univariate analysis (Table 6) for all 38 normalized genes and the predicted fusion parameter. Additionally, the odds ratios and p-values were reported with adjustment for ploidy status of the sample (diploid vs. tetraploid vs. aneuploid). As part of the Mayo Clinic standard practice, DNA ploidy was performed on all RRP cases. Therefore, since ploidy status has been previously indicated (Bostwick et al., *Arch. Pathol. Lab. Med.*, 124(7):995-1000 (2000) and Epstein et al., *Scand. J. Urol. Nephrol. Suppl.*, 216:34-63 (2005)) as potentially prognostic, it was evaluated and found to be significantly associated with case/control status. The odds ratio reflected the increased risk for each one unit increase in the assay, i.e., doubling of gene expression. Based on this analysis, the best univariate predictors were BIRC5, RRM2, and TOP2A. CDH10, also a significant predictor, had a negative coefficient suggesting a protective role. The other genes with a significant ($p \leq 0.05$) prognostic univariate effect were GRIN3A, COL2A1, NRP1, and SSTR1. When hierarchical clustering was performed for the normalized nucleic acids based on absolute correlation (FIG. 9), the nucleic acids BIRC5, RRM2, and TOP2A, which are the most important univariate nucleic acids, form a tight cluster and only one of them is retained in a multivariate model.

TABLE 6

Median Cts (normalized by RPS28), logistic regression coefficients and p-values for the genes examined by quantitative RT-PCR in the case/control study

| Nucleic acid | Cases median | Controls median | Adjusted for Ploidy | | Unadjusted | |
|---|---|---|---|---|---|---|
| | | | coefficient | p-value | coefficient | p-value |
| ADD2 | −14.8 | −14.3 | −0.13 | 0.15 | −0.08 | 0.32 |
| AMACR | −0.6 | −0.1 | −0.12 | 0.24 | −0.13 | 0.18 |
| B3GnT6 | −8.6 | −7.9 | −0.04 | 0.43 | −0.03 | 0.52 |
| BIRC5 | −8.0 | −9.2 | 0.47 | <0.001 | 0.52 | <0.001 |
| C20orf102 | −4.2 | −4.1 | 0.02 | 0.88 | −0.01 | 0.92 |
| C20orf22 | −6.1 | −6.1 | −0.12 | 0.28 | −0.09 | 0.43 |
| CADPS | −7.8 | −8.1 | −0.01 | 0.92 | 0.03 | 0.70 |
| CDH10 | −8.0 | −7.5 | −0.26 | 0.01 | −0.25 | 0.01 |
| CDH7 | −8.2 | −8.4 | 0.06 | 0.43 | 0.05 | 0.48 |
| Col10A1 | −7.5 | −7.5 | −0.09 | 0.64 | 0.04 | 0.83 |
| COL2A1 | −6.6 | −8.0 | 0.1 | 0.06 | 0.11 | 0.02 |
| DACH1 | −6.8 | −6.8 | −0.27 | 0.10 | −0.27 | 0.09 |
| DCAMKL1 | −5.1 | −4.9 | −0.1 | 0.45 | −0.07 | 0.61 |
| DDC | −9.9 | −12.0 | 0.06 | 0.29 | 0.08 | 0.13 |
| DSC54 | −5.8 | −6.2 | 0.02 | 0.86 | 0.02 | 0.83 |
| ERG | −5.6 | −5.5 | −0.04 | 0.58 | −0.03 | 0.70 |
| ETV1 | −7.6 | −7.6 | 0.1 | 0.34 | 0.12 | 0.23 |
| ETV4 | −8.3 | −8.4 | 0.03 | 0.75 | 0.01 | 0.91 |
| Fusion (−1, 0, 1)* Predicted | 29, 8, 62% | 37, 12, 47% | 0.29 | 0.12 | 0.27 | 0.12 |
| F5 | −6.6 | −7.1 | 0.07 | 0.42 | 0.1 | 0.26 |
| GRIN3A | −6.7 | −7.0 | 0.12 | 0.31 | 0.17 | 0.14 |
| HDAC9 | −10.6 | −10.7 | 0.05 | 0.60 | 0.07 | 0.45 |
| HOXC6 | −4.8 | −4.6 | −0.04 | 0.75 | −0.04 | 0.76 |
| HS2ST1 | −6.8 | −6.9 | 0.12 | 0.49 | 0.16 | 0.33 |
| KHDRBS3 | −5.4 | −5.9 | 0.18 | 0.15 | 0.22 | 0.06 |
| LTB | −6.7 | −6.8 | −0.04 | 0.70 | −0.05 | 0.63 |
| NRP1 | −3.1 | −3.6 | 0.46 | 0.01 | 0.42 | 0.02 |
| PCDHB10 | −6.9 | −6.9 | −0.01 | 0.96 | 0.07 | 0.56 |
| PHCA | −5.8 | −5.9 | −0.01 | 0.93 | 0.01 | 0.97 |
| PKIB | −5.7 | −5.8 | 0.09 | 0.50 | 0.14 | 0.28 |
| PPFIA2 | −6.9 | −7.3 | 0.01 | 0.86 | 0.02 | 0.84 |
| PTPRM | −4.8 | −4.4 | −0.22 | 0.09 | −0.17 | 0.17 |
| PTPRT | −5.7 | −5.9 | 0.02 | 0.82 | 0.03 | 0.75 |
| RAB6B | −6.8 | −7.3 | 0.1 | 0.52 | 0.15 | 0.32 |
| RRM2 | −9.7 | −10.9 | 0.36 | <0.001 | 0.4 | <0.001 |
| SDC2 | −5.2 | −5.1 | −0.19 | 0.21 | −0.13 | 0.37 |
| SERPINI | −8.7 | −8.6 | −0.02 | 0.85 | 0.04 | 0.76 |
| SLC3A1 | −5.1 | −5.0 | −0.02 | 0.91 | 0.04 | 0.83 |
| SSTR1 | −8.3 | −9.0 | 0.23 | 0.03 | 0.25 | 0.02 |
| TDO2 | −12.7 | −13.5 | 0.02 | 0.68 | 0.03 | 0.51 |

TABLE 6-continued

Median Cts (normalized by RPS28), logistic regression coefficients and p-values for the genes examined by quantitative RT-PCR in the case/control study

| Nucleic acid | Cases median | Controls median | Adjusted for Ploidy | | Unadjusted | |
|---|---|---|---|---|---|---|
| | | | coefficient | p-value | coefficient | p-value |
| TMEM45 | −7.5 | −8.0 | 0.12 | 0.29 | 0.14 | 0.22 |
| TOP2A | −7.0 | −8.0 | 0.54 | <0.001 | 0.58 | <0.001 |

*Based on ERG, ETV1 and ETV4. Percent negative[−1], undetermined[0], positive[1].

Multivariate Analysis Finds an Optimal Model

Figure 10:
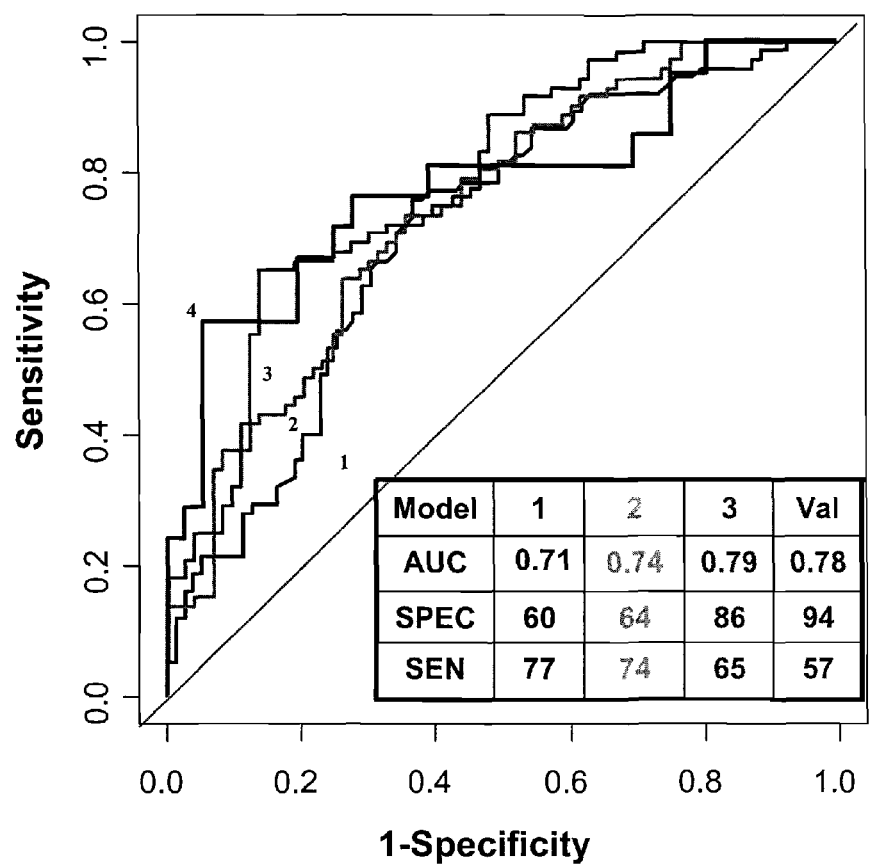
FIG. 10 is a graph plotting an ROC analysis based on logistic regression models for predicting systemic progression. Predictors in each model are: 1=TOP2a, 2=TOP2A+CDH10, 3=TOP2A+CDH10+Predicted Fusion, and 4=independent validation of model 3. The ROC curves for models 1, 2, 3, and 4, are all shown and are depicted by their model number. The inlayed table provides the AUC, specificity, and sensitivity for the optimal cutpoints for each step.

A forward stepwise selection process was used to define a three variable model for the prediction of prostate cancer outcome. The first variable included in the model was TOP2A as it possessed a significant p-value. With TOP2A in the model, BIRC5 and RRM2 were not significant predictors. The predictive performance of the model did not change significantly if either BIRC5 or RRM2 were selected as the first variable of the model. When any one of TOP2A, BIRC5, and RRM2 was selected as the first variable in the model, the other two nucleic acids lost significance, demonstrating these nucleic acids are interchangeable and suggesting they are related. The next most significant variable added to the model was CDH10. After adding CDH10 and TOP2A to the model, the significance of the fusion status (predicted fusion derived from high expression of ERG, ETV1, and ETV4) increased and became the most significant remaining parameter. Adding fusion status to TOP2A and CHD10 rendered the remaining nucleic acids insignificant. Each successive step of this modeling improved the corresponding Area Under the Curve (AUC) in the Receiver Operating Characteristic (ROC) plot. The AUC alone was 0.71. It was increased to 0.74 with CDH10, and increased to 0.79 with the predicted fusion parameter (FIG. 10). Ploidy remained a significant variable in this analysis. The final model (Table 7) consisting of predicted fusion, TOP2A, and CHD10 for ploidy was adjusted, and a significant change in the coefficients was not observed.

TABLE 7

Final logistic regression models predicting systemic progression.

| | Unadjusted for ploidy | | Adjusted for ploidy | |
|---|---|---|---|---|
| | Coefficient (SE) | p-value | Coefficient (SE) | p-value |
| Intercept | 0.19 | | −0.90 | |
| TOP2A | 0.73 (0.17) | 0.00002 | 0.69 (0.18) | 0.00009 |
| CDH10 | −0.64 (0.16) | 0.00005 | −0.67 (0.16) | 0.00004 |
| Pred fusion* | 0.94 (0.27) | 0.0057 | 0.97 (0.28) | 0.00054 |
| PLOIDY** | — | — | 0.76 (0.30) | 0.012 |

Figure 11:
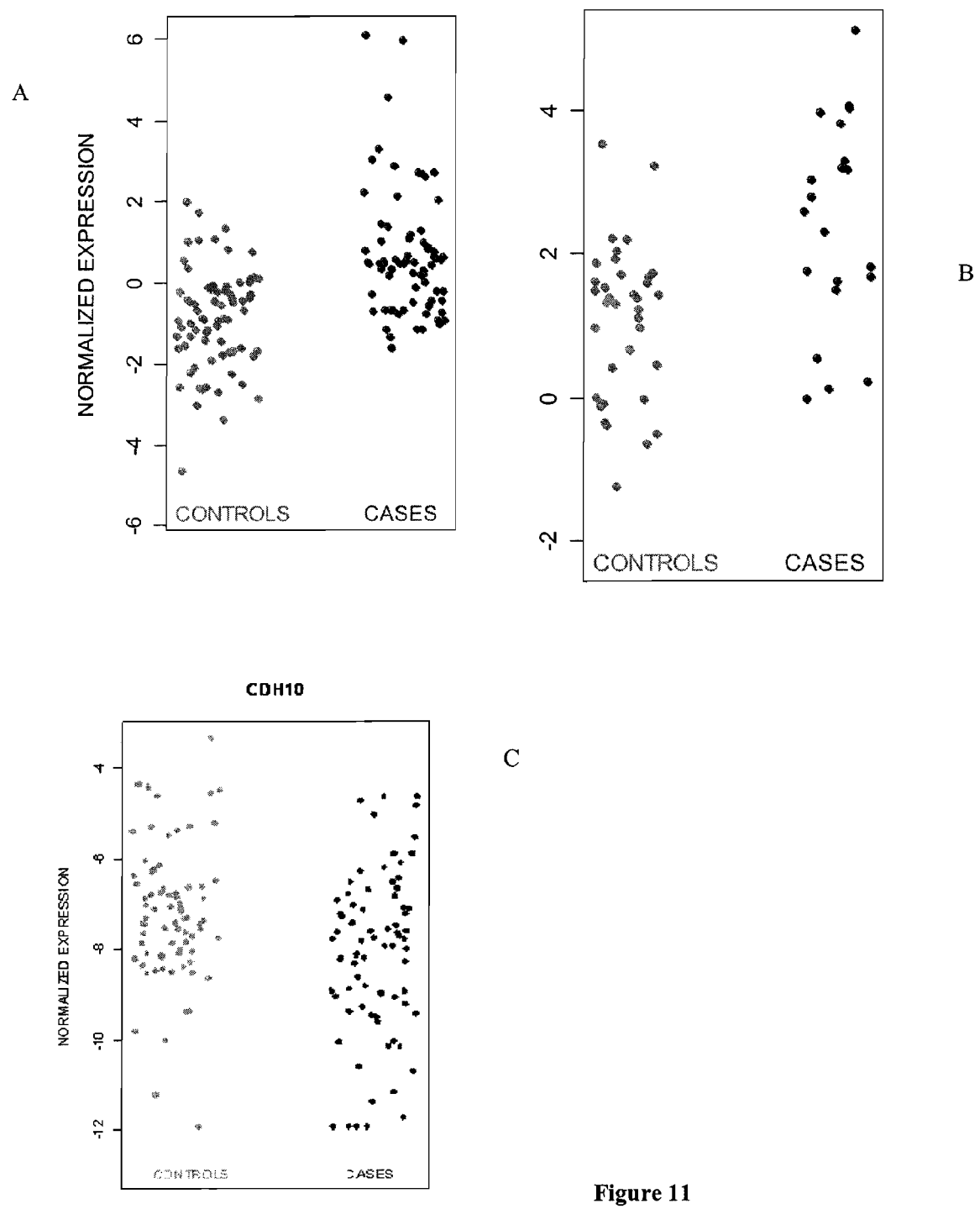
FIG. 11 contains scatter plots of the final variable model score for cases and controls of the training set (FIG. 11A) and the independent validation set (FIG. 11B) and a scatter plot of normalized expression values for CDH10 in cases and controls (FIG. 11C).

*Based on ERG, ETV1 and ETV4: −1 = negative, 0 = undetermined, 1 = positive.
**0 = diploid, 1 = tetraploid, 2 = aneuploid Using the predicted risk score from the regression model (Table 7), an optimal threshold for the identification of men with systemic progression was identified resulting in 65% sensitivity and 86% specificity. The score derived from the regression model was displayed, revealing the overall separation of the cases and the controls (FIG. 11A). Validation using frozen tumor tissue from a separate cohort of 57 high risk patients revealed a slight decrease in the AUC to 0.78. The ROC of the model in this independent validation set was also overlaid in FIG. 10, and the score derived from the regression model was displayed in FIG. 11B.

The results provided herein demonstrate that models can be used to distinguish men treated by RRP who develop systemic progression from men treated by RRP who do not develop systemic progression. A three-variable model, which includes TOP2A expression, CDH10 expression, and predicted TMPRSS2-(ERG, ETV1, or ETV4) fusion status, exhibits a sensitivity of 65% and specificity of 86%. The model was developed in a case control study of men matched on Gleason score, TNM stage, margin status, and preoperative serum PSA who did and did not develop systemic progression or die of prostate cancer. Survival curves by score group could not be generated due to the case/control design, wherein the event rate is pre-determined to be 50%. If the logistic score were applied prospectively, an increase in score of 0.7 (which is quite plausible) would imply a doubling in risk. For Gleason score 7, where the cumulative systemic progression rate at 10 years was 11%, this change in score could imply an overall increase in risk to around 20%.

In this case-control study, cases and controls were not matched for aneuploidy as this is not a standard pathologic assessment of prostate cancer in RRP specimens, and its association with prostate cancer outcome is debated. Ploidy generally correlates with other prognostic factors, such as Gleason score, tumor stage, and tumor volume: low-stage tumors are usually diploid, and high-stage tumors are usually non-diploid, and therefore some investigators have shown that there is no association of tumor ploidy with outcome in a multivariate model (Humphrey et al., Am. J. Surg. Pathol., 15(12):1165-70 (1991)). However, in a Mayo Clinic study, when patients with tumor that had spread beyond the prostate were examined, tumor ploidy was found to be significantly associated with progression (Robertson and Paulson, Acta Oncol., 30(2):205-7 (1991) and Winkler et al., Mayo Clin. Proc., 63(2):103-12 (1988)). In the Mayo Clinic practice, cancer ploidy is assessed on every RRP specimen, and therefore the significance of ploidy in the molecular model was investigated. It was found the ploidy was more weakly associated with cancer-specific outcome than the molecular markers but when the case-control was adjusted for ploidy, the coefficients of the model did not change significantly.

The samples evaluated in this study primarily consisted of patients of Caucasian descent. To obtain a more accurate assessment of prognostic performance in the population at large, a cohort study that includes proper minority population content can be used. Also, in the absence of an established assay to determine fusion status of the tumors, expression levels of the ETS gene family were used. This surrogate measure of fusion status has been applied in other studies (Demichelis et al., Oncogene, 26(31):4596-9 (2007)) and predicts the fusion status accurately.

Example 6

Diagnosing Prostate Cancer

The VOG-Δp and the pFC methods described in Example 3 were used to identify additional candidate nucleic acids for association with aggressiveness of prostate cancer. These nucleic acids were also evaluated with the same validation method that was described in Example 3 using the case-control group of patients that were matched with respect to clinical parameters, including margin, seminal vesicle, and/or nodal invasion. Both two-sided T-test and Wilcox tests were performed for these nucleic acids. These tests allow for protective nucleic acids with significant p-values also to pass threshold limits as well as nucleic acids with binary characteristics that would not look significant with the traditional t-test. Several nucleic acids passed at least one of the tests (Table 8). CDH10 is shown in bold because it is a protective gene (lower expression in cases than in controls). Also, TDO2 had a significant p-value with the Wilcox test and not with the t-test. This is attributed to the binary nature of its expression.

TABLE 8

Performance characteristics of additional nucleic acids.

| Nucleic acid name | p-value | |
|---|---|---|
| | T-test | Wilcox test |
| TDO2 | 0.3058 | 0.0368 |
| ST6GALNAC5, [ST6 (alpha-N-acetyl-neuraminyl-2,3-beta-galactosyl-1,3)-N-acetylgalactosaminide alpha-2,6-sialyltransferase 5] | 0.0306 | 0.0173 |
| COL2A1 | 0.0207 | 0.0092 |
| CDH10 | 0.0124 | 0.0071 |
| DIRAS2, [GTP-binding RAS-like 2] | 2.00E−04 | 1.00E−04 |
| BIRC5 | 1.00E−04 | 0 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for assessing prostate cancer, said method comprising:
   (a) detecting the presence of an elevated expression level for each of a majority of nucleic acids selected from the group consisting of KHDRBS3, NRP1, COL10A1, C20orf102, SSTR1, RRM2, F5, HSPC150, CDC2, TOP2A, SERPINI1, TDO2, GRIN3A, COL2A1, PCDHB10, ST6GALNAC5, DIRAS2, and BIRC5 nucleic acid by performing polymerase chain reactions that specifically amplify each of said majority of nucleic acids in a sample of nucleic acids from prostate tissue of a mammal, and
   (b) classifying said mammal as susceptible to a poor outcome.

2. The method of claim 1, wherein said mammal is a human.

3. The method of claim 1, wherein said poor outcome comprises systemic progression within five years of prostatectomy.

* * * * *